United States Patent
Schwartz et al.

(10) Patent No.: US 8,846,875 B2
(45) Date of Patent: Sep. 30, 2014

(54) PREPARATION AND/OR PURIFICATION OF OLIGONUCLEOTIDE CONJUGATES

(75) Inventors: David A. Schwartz, Encinitas, CA (US); Leopoldo G. Mendoza, Scottsdale, AZ (US)

(73) Assignee: Solulink, Inc., San Diego, CA (US)

( * ) Notice: Subject to any disclaimer, the term of this patent is extended or adjusted under 35 U.S.C. 154(b) by 0 days.

(21) Appl. No.: 13/578,752

(22) PCT Filed: Feb. 11, 2011

(86) PCT No.: PCT/US2011/024439
§ 371 (c)(1),
(2), (4) Date: Oct. 31, 2012

(87) PCT Pub. No.: WO2011/100493
PCT Pub. Date: Aug. 18, 2011

(65) Prior Publication Data
US 2013/0041140 A1    Feb. 14, 2013

Related U.S. Application Data

(60) Provisional application No. 61/282,434, filed on Feb. 12, 2010.

(51) Int. Cl.
*A61K 47/00* (2006.01)
*C07K 1/22* (2006.01)
*A61K 47/48* (2006.01)

(52) U.S. Cl.
CPC ........... *A61K 47/484* (2013.01); *C07K 2319/20* (2013.01); *C07K 2319/43* (2013.01); *C07K 2319/41* (2013.01); *C07K 1/22* (2013.01); *A61K 47/48507* (2013.01); *C07K 2319/21* (2013.01)

USPC ................. 530/391.1; 530/391.3; 530/391.5; 530/391.9; 530/391.7

(58) Field of Classification Search
CPC ..................................... A61K 47/484
See application file for complete search history.

(56) References Cited

U.S. PATENT DOCUMENTS

| | | | | |
|---|---|---|---|---|
| 4,650,675 | A * | 3/1987 | Borel et al. | 424/179.1 |
| 5,837,516 | A * | 11/1998 | Ballinger et al. | 435/221 |
| 6,379,699 | B1 * | 4/2002 | Virtanen et al. | 424/450 |
| 6,800,728 | B2 * | 10/2004 | Schwartz | 530/345 |
| 6,942,972 | B2 * | 9/2005 | Farooqui et al. | 435/5 |
| 7,102,024 | B1 * | 9/2006 | Schwartz et al. | 558/70 |
| 7,173,125 | B2 * | 2/2007 | Schwartz et al. | 536/26.26 |
| 7,309,567 | B1 * | 12/2007 | Mathis et al. | 435/6.1 |
| 7,462,689 | B2 * | 12/2008 | Schwartz | 530/345 |

(Continued)

OTHER PUBLICATIONS

Scouten, William H et al, Analytical Biochemistry, vol. 205, pp. 313-318, 1992, Reversible immobilization of antiobdies on magnetic beads.*

(Continued)

*Primary Examiner* — Albert Navarro
*Assistant Examiner* — Ginny Portner
(74) *Attorney, Agent, or Firm* — Jones Day

(57) ABSTRACT

Methods, systems and/or kits for the preparation, purification and isolation of oligonucleotide conjugates, comprising conjugation of modified antibodies or proteins with at least one modified oligonucleotide at greater than 80% efficiency to form oligonucleotide conjugates and isolating the oligonucleotide conjugates from the conjugation solution by binding the conjugates to an immobilized binder, wherein the binder may be a metal ion or an antibody.

30 Claims, 26 Drawing Sheets

(56) References Cited

U.S. PATENT DOCUMENTS

| | | | |
|---|---|---|---|
| 7,868,131 B2* | 1/2011 | Zhao et al. | 528/398 |
| 2003/0013857 A1* | 1/2003 | Schwartz | 530/408 |
| 2004/0018495 A1* | 1/2004 | Li | 435/6 |
| 2004/0038331 A1* | 2/2004 | Reddy et al. | 435/68.1 |
| 2004/0121382 A1* | 6/2004 | Liu et al. | 435/6 |
| 2005/0180997 A1* | 8/2005 | Benita et al. | 424/400 |
| 2007/0111222 A1 | 5/2007 | Chasin et al. | |
| 2008/0076139 A1* | 3/2008 | Singh | 435/7.23 |
| 2008/0171322 A1* | 7/2008 | Heyduk et al. | 435/6 |
| 2008/0221343 A1* | 9/2008 | Schwartz et al. | 549/550 |
| 2008/0249260 A1* | 10/2008 | Zhao et al. | 525/509 |
| 2009/0017004 A1* | 1/2009 | Zhao | 424/94.6 |
| 2009/0304581 A1* | 12/2009 | Scheinberg et al. | 424/1.53 |
| 2011/0086774 A1* | 4/2011 | Dunaway | 506/9 |
| 2012/0258880 A1* | 10/2012 | Schwartz et al. | 506/9 |
| 2012/0258881 A1* | 10/2012 | Schwartz et al. | 506/9 |
| 2012/0277113 A1* | 11/2012 | Huang | 506/9 |
| 2013/0035259 A1* | 2/2013 | Schwartz et al. | 506/16 |
| 2013/0123121 A1* | 5/2013 | Schwartz et al. | 506/9 |

OTHER PUBLICATIONS

Bailey, Ryan C et al, Journal of American Chemical Society, vol. 129, pp. 1959-1967, Published on web Jan. 30, 2007, DNA encoded antibody libraries: A Unified platform for multiplexed cell sorting and detection of genes and proteins.*

Solulink Conjugation Reagents and Kits, pp. 1-8, 2008.*

Pharmacia Superdex 200, product description, 1 page down loaded 2013.*

International Search Report dated May 20, 2011 for PCT/US2011/024439, 6 pages.

*Antibody-Oligonucleotide All-in-One Conjugation Kit User Manual*, Catalog No. A-9202-001, V.06.18.10, SoluLink (2009).

* cited by examiner

Stage 1
Modification of Amino-Oligonucleotide with Sulfo-S-4FB
(4 h)

1. Resuspend and verify oligo concentration (spectrophotometer)
2. Buffer exchange oligo on spin column
3. Modify amino-oligo with Sulfo-S-4FB and spin filter concentrate
4. Verify oligo concentration and determine 4FB MSR* (spectrophotometer)

Stage 2
Modification of Antibody with S-HyNic
(2.5 h)

1. Prepare antibody and verify concentration (spectrophotometer)
2. Buffer exchange on spin column
3. Modify antibody with S-HyNic
4. Buffer exchange on spin column

Stage 3
Conjugate Formation and Purification
(4 h)

1. Conjugate 4FB-labeled oligo to HyNic-labeled IgG
2. Affinity purify conjugate

*
 4FB MSR is an acronym for 4-formylbenzamide molar substitution ratio

FIGURE 15

PREPARATION AND/OR PURIFICATION OF OLIGONUCLEOTIDE CONJUGATES

CROSS-REFERENCE

This application is the National Phase application of International Application No. PCT/US2011/024439, filed Feb. 11, 2011, which designates the United States and was published in English, and further claims the benefit of priority from U.S. Provisional Application No. 61/282,434, filed Feb. 12, 2010. The foregoing related applications, in their entirety, are incorporated herein by reference.

Each of the following documents are incorporated herein by reference in its entirety:

U.S. Pat. Nos. 7,462,689; 6,800,728; 7,173,125; 6,686,461; 7,102,024; 6,911,535; 6,217,845; 5,753,520; 5,420,285; 5,679,778 and 5,206,370.

U.S. patent application Ser. No. 11/787,932, filed on Apr. 18, 2007, now U.S. Patent Publication No. 2008/0221343, published Sep. 11, 2008.

International Application No. PCT/US2001/09252, filed on Mar. 22, 2001, now World Publication No. WO 2001/70685; International Application No. PCT/US2001/023775, filed on Jul. 27, 2001, now World Publication No. WO 2002/010432 and International Application No. PCT/US2002/001161, filed on Jan. 16, 2002, now World Publication No. WO 2002/057422.

SoluLink manual, entitled "Antibody-Oligonucleotide All-in-One Conjugation Kit User Manual", Catalog No. A-9201-001, January 2010.

SEQUENCE LISTING

The instant application contains a Sequence Listing which has been submitted in ASCII format via EFS-Web and is hereby incorporated by reference in its entirety. Said ASCII copy, created on Apr. 5, 2011, is named 01283300.txt and is 968 bytes in size.

FIELD

The present disclosure relates to and may be applied to the preparation and/or purification of oligonucleotide conjugates.

BACKGROUND

Bioconjugates, such as protein-oligonucleotide conjugates, have been employed in a wide variety of molecular biology applications. For example, bioconjugates are used in biochemical assays and diagnostic assays to improve assay sensitivity. Bioconjugates, such as oligonucleotides conjugated to antibodies or enzymes, have been used as hybridization probes in immunoassays or as probes in the development of sensitive nucleic acid-based diagnostic assays. Such conjugates may be prepared by a variety of methods, such as glutaraldehyde crosslinking, maleimide-thiol coupling, isothiocyanate-amine coupling, hydrazone coupling, oxime coupling and Schiff base formation/reduction.

Despite the promise that bioconjugates hold in the area of biomedical research, such as improving assay sensitivity, simplifying nucleic acid detection schemes, clinical studies, development of both in vitro and in vivo diagnostic assays as well as in vivo therapies and the like, bioconjugates have not yet achieved their full potential in these molecular biology, biomedical and diagnostic applications. This deficiency is due, in part, to the less than quantitative preparation of bioconjugates, which may involve multiple steps and may require, for example, the protein, the oligonucleotide, or both, to be modified with the appropriate linking moiety and then purified before being combined and reacted with each other. Often the modification reaction may have a lengthy reaction time and may result in forming an unstable protein or oligomer intermediate that must be purified and used immediately. For these and other reasons, the yields to prepare these bioconjugates are highly variable and are greatly dependent on what techniques are used.

Another reason that has hindered the widespread use of bioconjugates, is the methods used to purify and isolate bioconjugates. Because of the inefficiencies in the conjugation chemistries used to prepare bioconjugates, often the resulting bioconjugate product may require several purification steps to obtain a purified bioconjugate, which can have a detrimental effect on the stability or activity of the final bioconjugate, its yield as well as be time consuming and expensive to prepare and/or purify.

Up to this point, the purification of bioconjugates has been accomplished using, for example, size exclusion chromatography, or occasionally, ion exchange chromatography. The requirement for HPLC chromatography for purification of bioconjugates has been a significant barrier for the routine use of bioconjugates, such as antibody-oligonucleotide bioconjugates in diagnostic assays. For these and other reasons, the costs of preparing and purifying bioconjugates have been expensive and have been difficult to make with reproducible results.

Therefore, there remains a great need for methods that provide a more efficient, robust, mild, simple and high-yielding purification of such bioconjugates to provide high purity bioconjugates for use in biomedical research and diagnostic assays.

Developments in conjugation chemistry have improved the efficiency of preparing bioconjugates. For example, SoluLink™ has disclosed conjugation chemistry that can be used to prepare an antibody-oligonucleotide bioconjugate with at least 80% efficiency. Accordingly, the preparation of bioconjugates using efficient conjugation chemistries has allowed for the ability to explore efficient, mild, robust, simple and high yielding purification methods to provide bioconjugates, such as antibody-oligonucleotide bioconjugates, in high yield having high purity to facilitate their use in molecular biology, biomedical and diagnostic research and application.

The present disclosure provides methods, systems and/or kits for the preparation, purification and/or isolation of bioconjugates that have been prepared via efficient conjugation chemistry, wherein the bioconjugate comprises at least one biomolecule conjugated to another biomolecule, for example, at least one oligonucleotide conjugated to an antibody or protein.

SUMMARY

Certain embodiments provide methods, for isolating antibody-oligonucleotide conjugates, comprising: i) introducing a modified antibody into a buffered solution; ii) conjugating the modified antibodies with at least one modified oligonucleotide at greater than 80% efficiency to form antibody-oligonucleotide conjugates and iii) isolating the antibody-oligonucleotide conjugates from the conjugation solution by binding the conjugates to an immobilized binder.

Certain embodiments provide methods, for isolating protein-oligonucleotide conjugates, comprising: i) introducing a modified protein into a buffered solution; ii) conjugating the modified protein with at least one modified oligonucleotide at greater than 80% efficiency to form protein-oligonucleotide conjugates and iii) isolating the protein-oligonucleotide conjugates from the conjugation solution by binding the conjugates to an immobilized binder.

These methods may be used as part of a kit and/or system of preparing, purifying and/or isolating antibody-oligonucleotide conjugates. In certain aspects, the immobilized binder may comprise a metal ion wherein the metal ion is a divalent metal ion, a transition metal ion, a divalent transition metal ion, or combinations thereof. In certain aspects, the transition metal ion is selected from the group comprising: nickel ion, zinc ion, copper ion, iron ion and cobalt ion. In certain aspects, the modified antibody may include a histidine-rich region as found naturally in eukaryotic cells. In certain aspects, the immobilized binder may further comprise an organic chelator selected from the group comprising: iminodiacetic acid, nitrilotriacetic acid and bicinchoninic acid. In certain aspects, the immobilized binder may comprise an immobilized antibody.

These methods may be used as part of a kit and/or system of preparing, purifying and/or isolating protein-oligonucleotide conjugates. In certain aspects, the immobilized binder may comprise a metal ion wherein the metal ion is a divalent metal ion, a transition metal ion, a divalent transition metal ion, or combinations thereof. In certain aspects, the transition metal ion is selected from the group comprising: nickel ion, zinc ion, copper ion, iron ion and cobalt ion. In certain aspects, the modified protein may include a histidine-rich region. In certain aspects, the immobilized binder may further comprise an organic chelator selected from the group comprising: iminodiacetic acid, nitrilotriacetic acid and bicinchoninic acid. In certain aspects, the immobilized binder may comprise an immobilized antibody.

In certain aspects, the modified antibody may comprise a molecular tag incorporated using protein engineering techniques. In certain aspects, the molecular tag may be selected from the group comprising: poly-histidine tag; Flag Tag; Myc-Tag, S-tag and/or a peptide tag. In certain aspects, the immobilized antibody may be complementary to the molecular tag that is bound to the modified antibody. In certain aspects, the immobilized antibody may be raised against the molecular tag that is bound to the modified antibody. The molecular tag may be a peptide tag. In certain aspects, the immobilized binder may be an antibody raised against the conjugative linker joining the modified antibody to the at least one modified oligonucleotide.

In certain aspects, the modified protein may comprise a molecular tag incorporated using protein engineering techniques. In certain aspects, the molecular tag may be selected from the group comprising: poly-histidine tag; Flag Tag; Myc-Tag, S-tag and/or a peptide tag. In certain aspects, the immobilized antibody may be complementary to the molecular tag that is bound to the modified protein. In certain aspects, the immobilized antibody may be raised against the molecular tag that is bound to the modified protein. The molecular tag may be a peptide tag. In certain aspects, the immobilized binder may be an antibody raised against the conjugative linker joining the modified protein to the at least one modified oligonucleotide.

In certain embodiments, the conjugating efficiency is greater than 85%, 90%, 92%, 95%, 96%, 97%, 98%, 98.5% or 99%. In certain embodiments, the conjugating efficiency is at least 85%, 90%, 92%, 95%, 96%, 97%, 98%, 98.5% or 99%.

In certain embodiments, the isolated antibody-oligonucleotide conjugates comprise on average at least 0.5 modified oligonucleotides. In certain aspects, the modified antibody is prepared from an IgG or IgM type antibody. In certain aspects, the modified antibody comprises an antibody that has been prepared by attaching at least one moiety comprising a reactive linker capable of conjugating to a modified oligonucleotide. This at least one moiety may be attached by a covalent bond. Furthermore, the at least one moiety may comprise a spacer group. Furthermore, the spacer group may comprise polymerized ethylene oxide. The spacer group may also be PEG or PEO.

In certain aspects, the modified antibody is prepared by attaching at least one moiety comprising a reactive linker capable of conjugating to a modified oligonucleotide. This at least one moiety may be attached by a covalent bond. The modified antibody may further comprise a molecular tag. Furthermore, the at least one moiety may comprise a spacer group. Furthermore, the spacer group may comprise polymerized ethylene oxide. The spacer group may also be PEG or PEO.

In certain aspects, the modified protein is prepared by attaching at least one moiety comprising a reactive linker capable of conjugating to a modified oligonucleotide. This, at least one moiety may be attached by a covalent bond. The modified protein may further comprise a molecular tag. Furthermore, the at least one moiety may comprise a spacer group. Furthermore, the spacer group may comprise polymerized ethylene oxide. The spacer group may also be PEG or PEO.

In certain embodiments, the isolated protein-oligonucleotide conjugates comprise on average at least 0.5 modified oligonucleotides. In certain aspects, the modified protein is prepared by solid phase protein synthesis. In certain aspects, the modified protein comprises a protein that has been prepared by attaching at least one moiety comprising a reactive linker capable of conjugating to a modified oligonucleotide during solid phase protein synthesis. This, at least one moiety may be attached by a covalent bond. Furthermore, the at least one moiety may comprise a spacer group. Furthermore, the spacer group may comprise polymerized ethylene oxide. The spacer group may also be PEG or PEO.

In certain embodiments, the at least one moiety may be HyNic. In certain aspects, the modified antibody may comprise a HyNic-modified antibody. In certain embodiments, the modified oligonucleotide may comprise a 4FB (4-formylbenzamide)-modified oligonucleotide. In certain aspects, the modified antibody may be an antibody that has been modified by attaching at least one moiety that is a reactive linker capable of conjugating to a modified oligonucleotide. The modified antibody may further comprise a molecular tag. In certain aspects, the immobilized antibody may be selective for the molecular tag that is bound to the modified antibody. In certain aspects, the modified antibody may comprise an antibody that has been further modified by attaching a histidine fusion peptide capable of chelating a metal ion. In certain embodiments, the immobilized binder may comprise a metal ion.

In certain embodiments, the at least one moiety may be HyNic. In certain aspects, the modified protein may comprise a HyNic-modified protein. In certain embodiments, the modified oligonucleotide may comprise a 4FB-modified oligonucleotide. In certain aspects, the modified protein may be a protein that has been modified by attaching at least one moiety that is a reactive linker capable of conjugating to a modified oligonucleotide. The modified protein may further comprise a molecular tag. In certain aspects, the immobilized antibody may be selective for the molecular tag that is bound to the modified protein. In certain aspects, the modified protein may comprise a protein that has been further modified by attaching a histidine fusion peptide capable of chelating a metal ion. In certain embodiments, the immobilized binder may comprise a metal ion.

In certain embodiments, the conjugate may be formed with a covalent linkage. Furthermore, in certain embodiments, the covalent linkage may be selected from the group comprising: an amide, an oxime, a hydrazone, a sulfide, an ether, an enol ether, a thiolether, an ester, a triazole and a disulfide. In certain aspects, the covalent linkage may comprise a hydrazone. In certain aspects, the hydrazone may be a bis-arylhydrazone. Furthermore, in certain aspects, the covalent linkage may be UV-traceable.

In certain embodiments, the methods disclosed may be mild, robust, more efficient, cost effective, simple and/or combinations thereof. In addition, such methods result in high-yielding purification of bioconjugates to provide high purity bioconjugates for use in biomedical applications and/or diagnostic assays.

In certain embodiments, the isolated antibody-oligonucleotide conjugates may comprise at least one modified oligonucleotide. In certain embodiments, the isolated antibody-oligonucleotide conjugates may comprise a composition of antibody-oligonucleotide conjugates having on average between 1.0 and 5, or between 1 and 2.5 modified oligonucleotides conjugated to the antibody. In certain embodiments, the methods disclosed yields at least 30-80%, 40-80%, 40-70%, 60-80% or 70-80% of the isolated antibody-oligonucleotide conjugates, with respect to starting modified antibody.

In certain embodiments, the isolated protein-oligonucleotide conjugates may comprise at least one modified oligonucleotide. In certain embodiments, the isolated protein-oligonucleotide conjugates may comprise a composition of protein-oligonucleotide conjugates having on average between 1.0 and 2.5 modified oligonucleotides conjugated to the protein. In certain embodiments, the methods disclosed yields at least 30-80%, 40-80%, 40-70%, 60-80% or 70-80% of the isolated protein-oligonucleotide conjugates, with respect to starting modified protein.

In certain embodiments, the antibody-oligonucleotide conjugates may comprise a detectable fluorophore. In certain aspects, the antibody-oligonucleotide conjugates may comprise at least one or at least two detectable fluorophores. In certain embodiments, the antibody-oligonucleotide conjugates may comprise a detectable poly-fluorophores.

In certain embodiments, the protein-oligonucleotide conjugates may comprise a detectable fluorophore. In certain aspects, the protein-oligonucleotide conjugates may comprise at least one or at least two detectable fluorophores. In certain embodiments, the protein-oligonucleotide conjugates may comprise a detectable poly-fluorophores.

In certain embodiments, the least a portion of the antibody-oligonucleotide conjugates may comprise two different modified oligonucleotides.

In certain embodiments, the least a portion of the protein-oligonucleotide conjugates may comprise two different modified oligonucleotides.

Certain embodiments provide methods, for isolating antibody-oligonucleotide conjugates, comprising: i) conjugating a modified antibody with at least one modified oligonucleotide to form antibody-oligonucleotide conjugates, wherein greater than 80% of the modified antibodies are conjugated; ii) adding the conjugation reaction mixture to a column having a stationary phase comprising a binder that has been immobilized to the stationary phase; iii) binding the antibody-oligonucleotide conjugates selectively to the immobilized binder; iv) eluting reaction components away from the bound antibody-oligonucleotide conjugates and v) isolating the antibody-oligonucleotide conjugates by releasing the bound, antibody-oligonucleotide conjugates with a displacing agent selective for the binder.

Certain embodiments provide methods, for isolating protein-oligonucleotide conjugates, comprising: i) conjugating a modified protein with at least one modified oligonucleotide to form protein-oligonucleotide conjugates, wherein greater than 80% of the modified proteins are conjugated; ii) adding the conjugation reaction mixture to a column having a stationary phase comprising a binder that has been immobilized to the stationary phase; iii) binding the protein-oligonucleotide conjugates selectively to the immobilized binder; iv) eluting reaction components away from the bound protein-oligonucleotide conjugates and v) isolating the protein-oligonucleotide conjugates by releasing the bound, protein-oligonucleotide conjugates with a displacing agent selective for the binder.

These methods may be used as part of a kit and/or system of preparing, purifying and/or isolating antibody-oligonucleotide conjugates. In certain embodiments, the conjugating efficiency may be greater than 85%, 90%, 92%, 95%, 96%, 97%, 98%, 98.5% or 99%. In certain embodiments, the conjugating efficiency may be at least 85%, 90%, 92%, 95%, 96%, 97%, 98%, 98.5% or 99%. In certain embodiments, the methods disclosed yields at least 30-80%, 40-80%, 40-70%, 60-80% or 70-80% of the isolated antibody-oligonucleotide conjugates, with respect to starting modified antibody.

These methods may be used as part of a kit and/or system of preparing, purifying and/or isolating protein-oligonucleotide conjugates. In certain embodiments, the conjugating efficiency may be greater than 85%, 90%, 92%, 95%, 96%, 97%, 98%, 98.5% or 99%. In certain embodiments, the conjugating efficiency may be at least 85%, 90%, 92%, 95%, 96%, 97%, 98%, 98.5% or 99%. In certain embodiments, the methods disclosed yields at least 30-80%, 40-80%, 40-70%, 60-80% or 70-80% of the isolated protein-oligonucleotide conjugates, with respect to starting modified protein.

In certain aspects, the stationary phase used may comprise a water insoluble support. In certain aspects, the stationary phase may be agarose and/or magnetic In certain aspects, the immobilized binder comprise a metal ion. Furthermore, the metal ion may be selected from the group comprising: nickel ion, zinc ion, copper ion, iron ion and/or cobalt ion.

In certain embodiments, the modified antibody includes a histidine-rich region.

In certain embodiments, the modified protein includes a histidine-rich region.

In certain aspects, the immobilized binder may comprise an immobilized antibody. In certain aspects, the modified antibody may further comprise a molecular tag. Furthermore, the immobilized antibody may be selective for the molecular tag that is bound to the modified antibody. In certain aspects, the modified protein may further comprise a molecular tag. Furthermore, the immobilized antibody may be selective for the molecular tag that is bound to the modified protein.

In certain embodiments, modified biomolecules are provided. These compounds are prepared, for example, by reaction of a biomolecule of interest with one of the functionalities of a bifunctional reagent. The modified biomolecules are available for conjugation or immobilization using the remaining functional group. Biomolecules for use herein include, but are not limited to, proteins including antibodies, glycoproteins, peptides, oligonucleotides, RNA and/or DNA.

In certain embodiments, modified solid supports, or substantially solid supports, are also provided, including, but not limited to, synthetic polymers, beads, glass, slides, metals and/or particles that have been modified by reaction with a bifunctional reagent to afford modified synthetic polymers, beads, latex, glass, slides, metals, including colloidal metals and/or particles that possess a hydrazino or oxyamino group. Combinations of modified solid supports, or substantially solid supports, are also contemplated. For example, these modified solid, or substantially solid, supports are useful in immobilization of biomolecules that possess or are modified to possess a carbonyl group. The immobilized biomolecules may also be used in diagnostic and/or therapeutic applications.

In certain embodiments, methods for purifying conjugates of biomolecules (for example, antibody-oligonucleotide conjugates) may involve metal chelation chromatography that utilizes the interaction of a metal ion, for example, $Ni^{+2}$ ion, $Zn^{+2}$ ion, $Cu^{+2}$ ion, $Fe^{+2}$ ion, or $Co^{+2}$ ion and the antibody. In certain embodiments, an aqueous mixture of antibody-oligonucleotide conjugates and free, or substantially free, modified-oligonucleotide, may be contacted with a water insoluble stationary phase which has the metal ion chelated to the phase. In certain embodiments, the conjugate chelates with the metal ion whereas neither of the specified free modified-oligonucleotide chelate. In certain embodiments, subsequent washing of the phase with a mild buffer may remove, or substantially remove, the unbound modified-oligonucleotide. In certain embodiments, the antibody-oligonucleotide conjugates may then be eluted from the phase and recovered in a form free, sufficiently free, or substantially free, of unconjugated modified-oligonucleotide.

BRIEF DESCRIPTION OF THE FIGURES

In order to facilitate a more detailed understanding of the nature of certain embodiments disclosed herein, exemplary embodiments of processes, systems, kits, preparations, methods, purifications, or combinations thereof, will now be described in further detail, by way of example only, with reference to the accompanying figures.

FIG. 15: The three stages of the conjugation process as summarized below. Additional details are illustrated in FIGS. 16, 17, and 18.

DETAILED DESCRIPTION

Figure 1:
FIG. 1 is a gel electrophoresis loading 400 ng of antibody with Sybr stain, containing the following lanes: Marker (lane 1); SFB-H1A (lane 2); HyNic-Bovine IgG (lane 3); Bovine IgG/H1A crude (lane 4) and Bovine IgG/H1A purified (lane 5), in accordance with certain embodiments.

Unless defined otherwise, the technical and scientific terms used herein have the same meaning as is commonly understood by one of skill in the art to which this disclosure belongs. In the event that there is a plurality of definitions for a term herein, those in this section prevail.

The term "synthetic molecule" may refer to a small molecule or polymer that is not naturally derived.

The term "biopolymer" may refer to a compound found in nature, a derivative of a compound found in nature, a synthetically modified analog of a compound found in nature, a genetically engineered analog of a compound found in nature, a genetically engineered modified analog of a compound found in nature, wherein the biopolymer may be made up of monomeric units. For example, biopolymers may include, but are not limited to, oligonucleotides, RNA, DNA, peptides, peptide nucleic acids (PNAs), proteins including antibodies, glycoproteins, enzymes, oligosaccharides and/or derivatives thereof. Examples of monomeric units include, but are not limited to, nucleotides, nucleosides, amino acids, PNA monomers, monosaccharides and derivatives thereof.

The term "biomolecule" may refer to a compound found in nature, a derivative of a compound found in nature, a synthetically modified analog of a compound found in nature, a genetically engineered analog of a compound found in nature, a genetically engineered modified analog of a compound found in nature. For example, biomolecules may include, but are not limited to, oligonucleotides, RNA, DNA, peptides, peptide nucleic acids (PNAs), proteins, antibodies, glycoproteins, enzymes, antigens, oligosaccharides, substrates for enzymes, substrates for nuclear receptors, genetically engineered peptides, genetically engineered proteins, genetically engineered antibodies and/or derivatives thereof.

The term "oligonucleotide" may refer to a nucleic acid, including, but not limited to, a ribonucleic acid (RNA), a deoxyribonucleic acid (DNA), a mixed ribonucleotide/deoxyribonucleotide; i.e., the oligonucleotide may include ribose or deoxyribose sugars or a mixture of both, and analogs thereof such as a protein nucleic acid (PNA), of various lengths, including chromosomes and genomic material, such as PCR products or sequencing reaction products, for example, DNA including double and single stranded forms. Oligonucleotides may sometimes be referred to as "oligo". Single stranded forms of the oligonucleotides are also provided. Alternatively, the oligonucleotide may include other 5-carbon or 6-carbon sugars, such as, for example, arabinose, xylose, glucose, galactose or deoxy derivatives thereof or any mixture of sugars. In certain embodiments, the oligonucleotide may refer to nucleic acid molecules of 2-2000 nucleosides in length. The oligonucleotide may be composed of naturally occurring nucleosides adenosine, guanosine, cytidine, thymidine and uridine, modified nucleosides, unnatural nucleosides, substituted nucleosides or unsubstituted nucleosides, purine or pyrimidine base or combinations thereof. Such purine and pyrimidine bases include, but are not limited to, natural purines and pyrimidines such as adenine, cytosine, thymine, guanine, uracil, or other purines and pyrimidines, such as isocytosine, 6-methyluracil, 4,6-di-hydroxypyrimidine, hypoxanthine, xanthine, 2,6-diaminopurine, 5-azacytosine, 5-methyl cystosine and the like. For example, the nucleosides may be joined by naturally occurring phosphodiester linkages or modified linkages, such as phosphorothioate linkages, methylphosphonate linkages and peptide backbones (peptide nucleic acids (PNA)).

The term "nucleobase" means a heterocyclic moiety that is found in naturally occurring oligonucleotides, including ribonucleic acids (RNA) and deoxyribonucleic acids (DNA) and analogs thereof, including deaza analogs. The nucleobase may include, but is not limited to, cytosines, uracils, adenines, guanines and thymines and analogs thereof including deaza analogs.

The term "amino acid" may refer to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlPip) refers to a mixture of the L- and D-isomers of the amino acid.

The term "conjugate" may represent a compound containing at least two components linked together. The individual components may be linked directly through one or more covalent bonds, or one or more ionic bonds, or by chelation, or mixtures thereof. The linkage, or conjugation, may include one or more spacer groups between the one or more linkages joining the one or more individual components, or may be between the individual component and the linkage. For example, the spacer group may include, but is not limited to an ethyleneoxide moiety, a polymer formed from repeating —($—CH_2—CH_2O—$)— moieties, such as polyethylene glycol (PEG), or polyethylene oxide (PEO). The individual components that may be linked together may include, but is not limited to biologically derived biopolymers, modified biopolymers, biologically derived biomolecules and synthetically derived molecules. For example, the conjugate may comprise a first component, such as a protein, that may be linked, i.e., conjugated, directly through one or more covalent bonds to a second component, such as an oligonucleotide, to form a conjugate. In certain embodiments, the linkage may be stable to thermolysis or hydrolysis or both. In certain embodiments, the linkage may be biocompatible. In certain embodiments, the spacer may be stable to thermolysis or hydrolysis or both. In certain embodiments, the spacer may be biocompatible.

The term "bioconjugate" may refer to a conjugate of at least two biomolecules, of at least two biopolymers or at least one biomolecule and at least one biopolymer. The bioconjugate may also include one or more linkages between the individual components that have been conjugated. The bioconjugate may also include one or more spacer groups between the one or more linkages joining the one or more individual components, or the spacer group may be between the individual component and the linkage. For example, the spacer group may include, but is not limited to an ethyleneoxide moiety, a polymer formed from repeating —($CH_2$—$CH_2O$—)— moieties, PEG or PEO.

The term "modified" may refer to a modification of a molecule, such as a biomolecule or a biopolymer, either by chemical synthesis, bio-engineering or the like. In certain embodiments, the molecule is modified by the attachment of a moiety, for example by a covalent bond, onto the molecule, such that once attached, the now modified molecule is capable of reacting with another molecule to form a conjugate. In certain embodiments, the moiety attached to the molecule to form the modified molecule includes a reactive group, or a linkable group available to link, i.e., conjugate, to another complementary reactive group attached to another molecule. In certain embodiments, the modified molecule, comprises a reactive group that is protected, and requires deprotection before being available to link, i.e., conjugate, to another reactive group attached to another molecule. In certain embodiments, the modification of a molecule may further comprise attaching a spacer group, a molecular tag, a fusion protein comprising a histidine rich region or combinations thereof.

The term "complementary reactive groups" represents those groups that, when reacted together, form a covalent linkage. For example, a hydrazino group may be complementary to a carbonyl derivative. For example, an oxyamino group may also be complementary to a carbonyl derivative. For example, an amino reactive group may refer to moieties that may react directly with amine-reactive moieties forming amide bonds. For example, a thiol reactive group may refer to moieties that may react directly with sulfhydryl-reactive groups forming stable sulfide bonds.

The term "linkage" may refer to the connection between two molecules, for example, the connection between two modified molecules. In certain embodiments, the linkage may be formed by the formation of a covalent bond. In certain embodiments, the covalent linkage may include, but is not limited to the formation of an amide bond, an oxime bond, a hydrazone bond, a triazole bond, a sulfide bond, an ether bond, an enol ether bond, an ester bond or a disulfide bond. In certain embodiments, the hydrazone bond may be, for example, a bis-arylhydrazone bond. In certain embodiments, the linkage may provide a UV-traceable characteristic that may be used to detect or quantify the amount of conjugate formed.

The term "fluorophore" may refer to a fluorescent compound. Fluorescence generally refers to the physical process in which light is emitted from the compound following absorption of radiation. Generally, the emitted light is of lower energy and longer wavelength than that absorbed. In certain embodiments, the fluorescence of the fluorophores used herein can be detected using standard techniques to measure fluorescence.

The term "derivative of a compound" may include, for example, a salt, ester, enol ether, enol ester, solvate or hydrate thereof that may be prepared by those of skill in this art using known methods for such derivatization. Salts may include, but are not limited to, amine salts; alkali metal salts, such as but not limited to lithium, potassium and sodium; alkali earth metal salts, such as but not limited to barium, calcium and magnesium; transition metal salts, such as but not limited to nickel, zinc, copper, cobalt, and iron and other metal salts, such as but not limited to sodium hydrogen phosphate and disodium phosphate; and also may include, but is not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. For example, esters may include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Enol ethers may include, but are not limited to, derivatives of formula $C=C(OR)$ where R is hydrogen, alkyl, alkenyl, alkynyl, aryl, heteroaryl, aralkyl, heteroaralkyl, cycloalkyl or heterocyclyl. Enol esters may include, but are not limited to, derivatives of formula $C=C(OC(O)R)$ where R is hydrogen, alkyl, alkenyl, alkynyl, aryl, heteroaryl, aralkyl, heteroaralkyl, cycloalkyl or heterocyclyl. Solvates and hydrates are complexes of a compound with one or more solvent or water molecule, for example, 1 to about 100, 1 to about 10, 1 to about 2, 3 or 4, solvent or water molecules.

The term "molecular tag" may refer to a peptide sequence that is attached to a molecule. For example, in certain embodiments, the molecular tag is a peptide sequence that is recognized as an antigen by an antibody. In certain embodiments, the molecular tag may include, but is not limited to, a polyhistidine tag, for example, a Flag Tag, a c-Myc-Tag, an S-tag or a peptide tag that an antibody has been raised against. In certain embodiments, the molecular tag may be attached to a molecule by synthetic means, by utilization of recombinant methodologies, genetic engineering, or combinations thereof. In certain embodiments, the molecular tag is a cloned short stretch of polyhistidines that is attached either onto the amino or carboxy terminus of a protein. In certain embodiments, the molecular tag may be recognized by an antibody. In certain embodiments, the molecular tag may form a chelate with a metal ion. For example, in certain embodiments, the molecular tag may be a poly-histidine tag that may form a chelate with a metal ion.

It is to be understood that, in certain embodiments, the compounds provided herein may contain chiral centers. Such chiral centers may be of either the (R) or (S) configuration, or may be mixtures thereof. For example, the compounds provided herein may be enantiomerically pure, diastereomerically pure or stereoisomerically pure. In certain embodiments, the compounds provided herein may be stereoisomeric mixtures or diastereomeric mixtures. For example, in the case of amino acid residues, each residue may be of either the L or D form. The preferred configuration for naturally occurring amino acid residues is L.

In certain embodiments, a method for isolating antibody-oligonucleotide conjugates is provided. In certain embodiments, an antibody-oligonucleotide conjugates is isolated, comprising: i) introducing a modified antibody into a buffered solution; ii) conjugating the modified antibodies with at least one modified oligonucleotide at greater than 80% efficiency to form antibody-oligonucleotide conjugates and iii) isolating the antibody-oligonucleotide conjugates from the conjugation solution by binding the conjugates to an immobilized binder. The method may comprise conjugation at greater than 85% efficiency, for example, greater than 90%, greater than 95% or greater than 98% efficiency to form antibody-oligonucleotide conjugates.

In certain embodiments, a method for isolating protein-oligonucleotide conjugates is provided. In certain embodiments, an protein-oligonucleotide conjugates is isolated, comprising: i) introducing a modified protein into a buffered solution; ii) conjugating a molecular tag to the protein; iii) conjugating the modified proteins with at least one modified oligonucleotide at greater than 80% efficiency to form protein-oligonucleotide conjugates and iv) isolating the protein-oligonucleotide conjugates from the conjugation solution by binding the conjugates to an immobilized binder. The method may comprise conjugation at greater than 85% efficiency, for example, greater than 90%, greater than 95% or greater than 98% efficiency to form protein-oligonucleotide conjugates.

In certain embodiments, the modified oligonucleotide may be prepared by reacting with a moiety that is a bifunctional molecular reagent containing a first reactive component that forms a covalent bond with the oligonucleotide and a second reactive component that may form a linkage with a complementary reactive component on a modified antibody or a modified protein or a tagged antibody or a tagged protein or other biomolecule. In certain embodiments, the second reactive component may be protected such that it will not react until removed following incorporation onto the oligonucleotide.

In certain embodiments, the modified oligonucleotide may be prepared by incorporating amino groups either 3', 5' or internally using methods and reagents known to those of skill in the art. For example, the modified oligonucleotide may be prepared by reacting with a moiety that is a bifunctional molecular reagent, such as a aromatic aldehyde or ketone, aromatic hydrazino or oxyamino modification reagent, to incorporate a hydrazino or oxyamino function respectively.

In certain embodiments, the modified oligonucleotide may be prepared by post-synthetically modification of oligonucleotides prepared via polymerases or reverse transcriptases with nucleoside triphosphates possessing an aromatic aldehyde, aromatic hydrazine, oxyamino or an amino group. For example, the modified oligonucleotide may be prepared by post-synthetically modification of oligonucleotides by incorporation of an aromatic aldehyde or ketone, aromatic hydrazino or oxyamino group using a moiety that is a bifunctional molecular reagent, such as a aromatic aldehyde or ketone, aromatic hydrazino or oxyamino reagent.

In certain embodiments, the modified antibodies are prepared from antibodies that are derived from eukaryotic cells. In certain embodiments, the modified antibodies are prepared from antibodies that are derived from prokaryotic cells. In certain embodiments, the modified antibody includes a molecular tag. In certain embodiments, the modified antibodies are prepared from antibodies that contain a histidine rich sequence near the hinge region. In certain embodiments, the modified antibodies are prepared from antibodies that are exclusive of, i.e., do not contain a histidine rich sequence near the hinge region that has an a molecular post-synthetically incorporated.

In certain embodiments, the phosphorus-containing moieties of the modified oligonucleotides may contain, for example, a phosphate, phosphonate, alkylphosphonate, aminoalkyl phosphonate, thiophosphonate, phosphoramidate, phosphorodiamidate, phosphorothioate, phosphorothionate, phosphorothiolate, phosphoramidothiolate and phosphorimidate. The phosphorus-containing moieties of the modified oligonucleotides may be modified with a cationic, anionic or zwitterionic moiety. The modified oligonucleotides may also contain backbone linkages which do not contain phosphorus, such as carbonates, carboxymethyl esters, acetamidates, carbamates, acetals and the like.

In certain embodiments, the modified antibody comprises an antibody that includes a histidine-rich region, for example, an antibody having a histidine-rich region near the hinge region of the antibody. The modified antibody may comprise an antibody that is exclusive of having a histidine-rich region. The modified antibody may comprise an antibody that is of the IgG type antibody or the IgM type antibody. The modified antibody may comprise one or more molecular tags, for example, but not limited to, a poly-histidine tag, a Flag Tag, a c-Myc-Tag or a peptide tag that an antibody has been raised against. The modified antibody may comprise a poly-histidine fusion protein. The modified antibody may comprise one or more spacer groups, for example, such as a polyethylene glycol (PEG) or a polyethylene oxide group (PEO). The modified antibody may comprise one or moieties that include a reactive group, for example, a reactive group that may form a covalent bond when reacted with a complementary reactive group that may be part of a modified oligonucleotide. The modified antibody may be, for example, a HyNic or 4FB-modified antibody.

In certain embodiments, the modified protein comprises a protein that includes a histidine-rich region, for example, a protein having a histidine-rich region incorporated during solid phase synthesis. The modified protein may comprise an protein that is exclusive of having a histidine-rich region. The modified protein may comprise one or more molecular tags, for example, but not limited to, a poly-histidine tag, a Flag Tag, a c-Myc-Tag or a peptide tag that an antibody has been raised against. The modified protein may comprise a poly-histidine fusion protein. The modified protein may comprise one or more spacer groups, for example, such as a polyethylene glycol (PEG) or a polyethylene oxide group (PEO). The modified protein may comprise one or moieties that include a reactive group, for example, a reactive group that may form a covalent bond when reacted with a complementary reactive group that may be part of a modified oligonucleotide. The modified protein may be, for example, a HyNic or 4FB-modified protein.

In certain embodiments, at least one modified oligonucleotide may comprise one or more oligonucleotides that have been modified, for example, at least two modified oligonucleotides, at least three, at least four modified oligonucleotides. The at least one modified oligonucleotide may comprise two different modified oligonucleotides, for example, three different modified nucleotides or four different modified oligonucleotides. The at least one modified oligonucleotide may comprise one or more spacer groups, for example, a PEG or PEO group. The modified oligonucleotide may comprise one or moieties that include a reactive group, for example, a reactive group that may form a covalent bond when reacted with a complementary reactive group that may be part of a modified antibody. The modified oligonucleotide may be, for example, a 4FB-modified oligonucleotide.

In certain embodiments, the stoichiometry of the conjugation reaction to form the antibody-oligonucleotide conjugates comprises one equivalent of modified antibody and at least 1.0 equivalents of modified oligonucleotide, for example, at least 1.5 equivalents, at least 2.0 equivalents, at least 2.5 equivalents, at least 3.0 equivalents, at least 3.5 equivalents at least 4.0 equivalents or at least 5.0 equivalents of modified oligonucleotide. In certain embodiments, the stoichiometry of the conjugation reaction to form the antibody-oligonucleotide conjugates comprises one equivalent of modified antibody and between about 1.0 and about 2.0 of modified oligonucleotide, for example, between about 1.5 and about 2.5 equivalents, between about 2.0 and about 2.5 equivalents, between about 2.0 and about 3.0 equivalents, between about 2.5 and about 3.5 equivalents, between about 3.0 and about 3.5 equivalents, between about 3.0 and about 4.0 equivalents between about 3.5 and about 4.5 equivalents or between 4.5 and 5.5 equivalents modified oligonucleotide. The stoichiometry of the conjugation reaction may be adjusted to form antibody-oligonucleotide conjugates that retain sufficient immunoreactivity of the antibody that has been conjugated.

In certain embodiments, the stoichiometry of the conjugation reaction to form the protein-oligonucleotide conjugates comprises one equivalent of modified protein and at least 1.0 equivalents of modified oligonucleotide, for example, at least 1.5 equivalents, at least 2.0 equivalents, at least 2.5 equivalents, at least 3.0 equivalents, at least 3.5 equivalents, at least 4.0 equivalents or at least 5.0 equivalents of modified oligonucleotide. In certain embodiments, the stoichiometry of the conjugation reaction to form the protein-oligonucleotide conjugates comprises one equivalent of modified protein and between about 1.0 and about 2.0 of modified oligonucleotide, for example, between about 1.5 and about 2.5 equivalents, between about 2.0 and about 2.5 equivalents, between about 2.0 and about 3.0 equivalents, between about 2.5 and about 3.5 equivalents, between about 3.0 and about 3.5 equivalents, between about 3.0 and about 4.0 equivalents between about 3.5 and about 4.5 equivalents or between 4.5 and 5.5 equivalents modified oligonucleotide.

In certain embodiments, the antibody-oligonucleotide conjugates may be the conjugation product of one modified antibody and on average between 1.0 and 2.0 modified oligonucleotides that have conjugated to the modified antibody. For example, the antibody-oligonucleotide conjugates may be the conjugation product of one modified antibody and on average between 0.5 and 1.0, 1.0 and 2.0 modified oligonucleotides that have conjugated to the modified antibody, for example, on average between 1.5 and 2.5, between 2.0 and 2.5, between 2.0 and 3.0, between 2.5 and 3.5, between 2.5 and 3.0, between 3.0 and 4.0, between 3.0 and 3.5 or between 3.5 and 4.5 modified oligonucleotides that have conjugated to the modified antibody.

In certain embodiments, the protein-oligonucleotide conjugates may be the conjugation product of one modified protein and on average between 1.0 and 2.0 modified oligonucleotides that have conjugated to the modified protein. For example, the protein-oligonucleotide conjugates may be the conjugation product of one modified protein and on average between 0.5 and 1.0, 1.0 and 2.0 modified oligonucleotides that have conjugated to the modified protein, for example, on average between 1.5 and 2.5, between 2.0 and 2.5, between 2.0 and 3.0, between 2.5 and 3.5, between 2.5 and 3.0, between 3.0 and 4.0, between 3.0 and 3.5 or between 3.5 and 4.5 modified oligonucleotides that have conjugated to the modified protein.

In certain embodiments, the antibody-oligonucleotide conjugates provided may be a mixture of antibody-oligonucleotide conjugates having modified oligonucleotides that have been conjugated to the modified antibody, but wherein the linkage points of the oligonucleotides to the antibody are not uniformly identical across the entire sample. For example, a prepared, purified and isolated antibody-oligonucleotide conjugates sample may have one antibody-oligonucleotide conjugate that has one set of linkage points for each of the oligonucleotides conjugated to the antibody and the same sample may have a different antibody-oligonucleotide conjugate that has a similar number of oligonucleotides conjugated to that antibody, but having a different set of linkage points for each of those oligonucleotides conjugated.

In certain embodiments, the protein-oligonucleotide conjugates provided may be a mixture of protein-oligonucleotide conjugates having modified oligonucleotides that have been conjugated to the modified protein, but wherein the linkage points of the oligonucleotides to the protein are not uniformly identical across the entire sample. For example, a prepared, purified and isolated protein-oligonucleotide conjugates sample may have one protein-oligonucleotide conjugate that has one set of linkage points for each of the oligonucleotides conjugated to the protein and the same sample may have a different protein-oligonucleotide conjugate that has a similar number of oligonucleotides conjugated to that protein, but having a different set of linkage points for each of those oligonucleotides conjugated.

In certain embodiments, the antibody-oligonucleotide conjugates or protein-oligonucleotide conjugates may be purified and/or isolated by binding to an immobilized binder. The immobilized binder may comprise a metal ion, for example, a divalent metal ion, such as a transition metal ion. The metal ion may include, but is not limited to, a nickel ion, a zinc ion, a copper ion, an iron ion or a cobalt ion. The metal ion may be immobilized by chelation to a stationary phase in a column. The stationary phase may comprise an organic chelator that immobilizes and/or binds the metal ion. For example, the organic chelator may be selected from the group that includes, but is not limited to, iminodiacetic acid, nitrilotriacetic acid and/or bicinchoninic acid. The stationary phase may be a water insoluble support, for example, the stationary phase may be agarose.

In certain embodiments, the immobilized binder may comprise an immobilized antibody. The immobilized antibody may recognize and bind a portion of the modified antibody and/or a portion of the antibody-oligonucleotide conjugates. The immobilized antibody may recognize and bind a modified antibody comprising a molecular tag, wherein the immobilized antibody is an antibody that has been raised to include that particular molecular tag. The immobilized antibody may recognize and bind the linkage formed during the conjugation reaction of the modified antibody and the modified oligonucleotide, wherein the immobilized antibody is an antibody that has been raised to include that particular conjugation linkage.

In certain embodiments, the immobilized binder may comprise an immobilized protein or aptamer. The immobilized protein or aptamer may recognize and bind a portion of the modified antibody and/or a portion of the antibody-oligonucleotide conjugates. The immobilized protein may be Protein A or Protein G (native or recombinant). Protein A is a 40-60 kDa MSCRAMM surface protein originally found in the cell wall of the bacteria *Staphylococcus aureus* binds with the Fc region of immunoglobulins through interaction with the heavy chain. Protein G is a 65 kDa protein that also binds the Fc region. The native molecule also binds albumin, however, because serum albumin is a major contaminant of antibody sources, the albumin binding site has been removed from recombinant forms of Protein G. Following binding and washing to remove non-conjugated oligonucleotide the antibody-oligonucleotide conjugate is released from the binding protein using 0.1 M glycine, pH 2-3 and immediately high-ionic strength alkaline buffer such as 1 M phosphate or 1 M Tris (pH 7.5-9).

In certain embodiments, the immobilized binder may comprise an immobilized antibody. The immobilized antibody may recognize and bind a portion of the modified protein and/or a portion of the protein-oligonucleotide conjugates. The immobilized antibody may recognize and bind a modified protein comprising a molecular tag, wherein the immobilized antibody is an antibody that has been raised to include that particular molecular tag. The immobilized antibody may recognize and bind the linkage formed during the conjugation reaction of the modified protein and the modified oligonucleotide, wherein the immobilized antibody is an antibody that has been raised to include that particular conjugation linkage.

In certain embodiments, the antibody-oligonucleotide conjugates may be purified and/or isolated by adding the conjugation reaction mixture to a column having a stationary phase comprising a binder that has been immobilized or substantially immobilized, to the stationary phase. The immobilized binder may comprise an immobilized antibody bound to the stationary phase. The immobilized binder may comprise a metal ion, for example, a divalent metal ion, such as a transition metal ion. The metal ion may be immobilized by chelation to a stationary phase in a column. The metal ion may include, but is not limited to, a nickel ion, a zinc ion, a copper ion, an iron ion or a cobalt ion.

In certain embodiments, the protein-oligonucleotide conjugates may be purified and/or isolated by adding the conjugation reaction mixture to a column having a stationary phase comprising a binder that has been immobilized, or substantially immobilized, to the stationary phase. The immobilized binder may comprise an immobilized antibody bound to the stationary phase. The immobilized binder may comprise a metal ion, for example, a divalent metal ion, such as a transition metal ion. The metal ion may be immobilized by chelation to a stationary phase in a column. The metal ion may include, but is not limited to, a nickel ion, a zinc ion, a copper ion, an iron ion or a cobalt ion.

In certain embodiments, the method of purifying and/or isolating the antibody-oligonucleotide conjugates may be by selectively binding the conjugates to a binder that is immobilized or substantially immobilized, on a stationary phase, eluting the reaction components away from the bound conjugate and then releasing the antibody-oligonucleotide conjugates by adding a displacing agent that is selective for the immobilized binder. The method for isolating antibody-oligonucleotide conjugates, comprises: i) conjugating a modified antibody with at least one modified oligonucleotide to form antibody-oligonucleotide conjugates, wherein greater than 80% of the modified antibodies are conjugated; ii) adding the conjugation reaction mixture to a column having a stationary phase comprising a binder that has been immobilized to the stationary phase; iii) binding the antibody-oligonucleotide conjugates selectively to the immobilized binder; iv) eluting reaction components away from the bound antibody-oligonucleotide conjugates and v) isolating the antibody-oligonucleotide conjugates by releasing the bound antibody-oligonucleotide conjugates with a displacing agent selective for the binder. The immobilized binder may be a metal ion and the displacing agent may be a solution comprising a chelator for the metal, for example, EDTA. The immobilized binder may be an immobilized antibody and the displacing agent may be a solution comprising a molecular tag that is recognized by the immobilized antibody.

In certain embodiments, the method of purifying and/or isolating the protein-oligonucleotide conjugates may be by selectively binding the conjugates to a binder that is immobilized or substantially immobilized, on a stationary phase, eluting the reaction components away from the bound conjugate and then releasing the protein-oligonucleotide conjugates by adding a displacing agent that is selective for the immobilized binder. The method for isolating protein-oligonucleotide conjugates, comprises: i) conjugating a modified protein with at least one modified oligonucleotide to form protein-oligonucleotide conjugates, wherein greater than 80% of the modified proteins are conjugated; ii) adding the conjugation reaction mixture to a column having a stationary phase comprising a binder that has been immobilized to the stationary phase; iii) binding the protein-oligonucleotide conjugates selectively to the immobilized binder; iv) eluting reaction components away from the bound protein-oligonucleotide conjugates and v) isolating the protein-oligonucleotide conjugates by releasing the bound protein-oligonucleotide conjugates with a displacing agent selective for the binder. The immobilized binder may be a metal ion and the displacing agent may be a solution comprising a chelator for the metal, for example, EDTA. The immobilized binder may be an immobilized antibody and the displacing agent may be a solution comprising a molecular tag that is recognized by the immobilized antibody.

In certain embodiments, the method of purifying and/or isolating the antibody-oligonucleotide conjugates may be mild, robust, simple, high yielding or combinations thereof. For example, the method may yield at least 30% isolated antibody-oligonucleotide conjugates, with respect to starting modified antibody. In other methods, the yield may be at least 40%, at least 50%, at least 65%, at least 70%, at least 75%, at least 80%, at least 85%, at least 90% or at least 95% isolated antibody-oligonucleotide conjugates, with respect to starting modified antibody.

In certain embodiments, the method of purifying and/or isolating the protein-oligonucleotide conjugates may be mild, robust, simple, high yielding or combinations thereof. For example, the method may yield at least 20% isolated protein-oligonucleotide conjugates, with respect to starting modified protein. In other methods, the yield may be at least 30%, at least 40%, at least 50%, at least 65%, at least 70%, at least 75%, at least 80%, at least 85%, at least 90% or at least 95% isolated protein-oligonucleotide conjugates, with respect to starting modified protein.

In certain embodiments, the method of purifying and/or isolating the antibody-oligonucleotide conjugates may provide more than one process by which to bind and release the antibody-oligonucleotide conjugates. The formed antibody-oligonucleotide conjugates may comprise a histindine-rich region included in the hinge region of the antibody, which may, for example, be bound by chelating to a metal ion immobilized on a column, and the formed antibody-oligonucleotide conjugates may further comprise a molecular tag that is recognized and may be bound by an antibody, for example, an antibody immobilized on a stationary phase. The formed antibody-oligonucleotide conjugates may comprise an antibody that is exclusive of, i.e., does not include a histidine-rich region and the formed antibody-oligonucleotide conjugates may further comprise a molecular tag that is recognized and may be bound by an antibody, for example, an antibody immobilized on a stationary phase, and wherein the molecular tag may also be bound by chelating to a metal ion. For example, the molecular tag may be a histidine-rich His-6 tag (SEQ ID NO: 1).

In certain embodiments, the method of purifying and/or isolating the protein-oligonucleotide conjugates may provide more than one process by which to bind and release the protein-oligonucleotide conjugates. The formed protein-oligonucleotide conjugates may comprise a histindine-rich region, which may, for example, be bound by chelating to a metal ion immobilized on a column and the formed protein-oligonucleotide conjugates may further comprise a molecular tag that is recognized and may be bound by an antibody, for example, an antibody immobilized on a stationary phase. The formed protein-oligonucleotide conjugates may comprise a protein that is exclusive of, i.e., does not include a histidine-rich region, and the formed protein-oligonucleotide conjugates may further comprise a molecular tag that is recognized and may be bound by an antibody, for example, an antibody immobilized on a stationary phase, and wherein the molecular tag may also be bound by chelating to a metal ion. For example, the molecular tag may be a histidine-rich His-6 tag (SEQ ID NO: 1).

In certain embodiments, the antibody-oligonucleotide conjugates may comprise one or more detectable fluorophores. For example, the antibody-oligonucleotide conjugates may comprise two or more different modified oligonucleotides that have conjugated to the antibody, where in each modified oligonucleotide comprises a different fluorophore. The antibody-oligonucleotide conjugates may form a fluorophore during the conjugation reaction.

In certain embodiments, the protein-oligonucleotide conjugates may comprise one or more detectable fluorophores. For example, the protein-oligonucleotide conjugates may comprise two or more different modified oligonucleotides that have conjugated to the protein, where in each modified oligonucleotide comprises a different fluorophore. The protein-oligonucleotide conjugates may form a fluorophore during the conjugation reaction.

Figure 9:
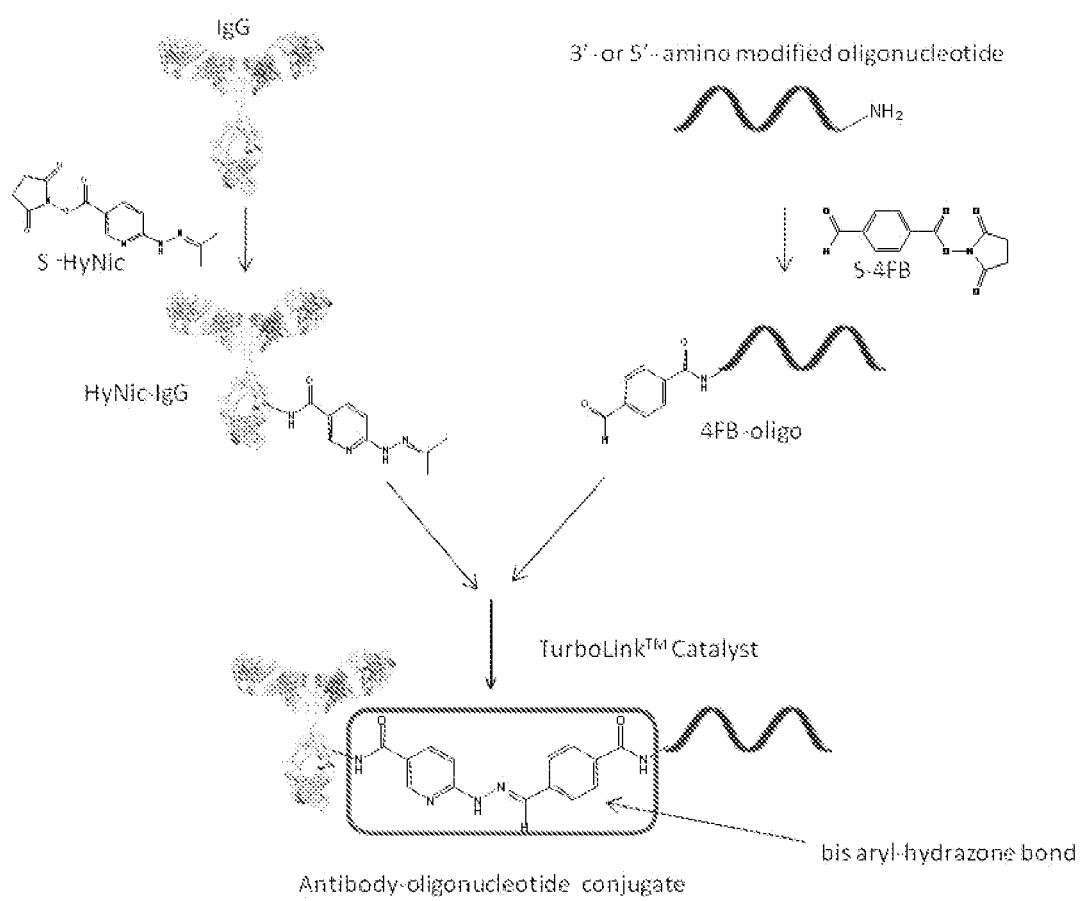
FIG. 9: Conjugation of HyNic-modified antibody with 4FB-oligonucleotide, in accordance with certain embodiments.

In certain embodiments, the antibody-oligonucleotide conjugates may be formed by the conjugation reaction as depicted in FIG. 9. For example, an amine group of an antibody, for example, of the IgG type, may react with the heterobifunctional reactive moiety succinimidyl 6-hydrazinonicotinate acetone hydrazone (S-HyNic) to form the modified antibody, called HyNic-IgG. Separately, an oligonucleotide is modified with the heterobifunctional reactive reagent succinimidyl 4-formylbenzoate (S-4FB) to form the modified oligonucleotide, called 4FB-oligonucleotide. The conjugation reaction involves the addition of at least one equivalent of the 4FB-oligonucleotide to the HyNic-IgG, for example, with no catalyst or in the presence of a catalyst, such as TurboLink™ Catalyst, 10 mM aniline or similar aromatic amine, to form an antibody-oligonucleotide conjugate. In this particular figure, the conjugation reaction involved the formation of a hydrazone bond, to prepare an antibody-oligonucleotide conjugate having a bis-aryl-hydrazone bond.

Figure 10:
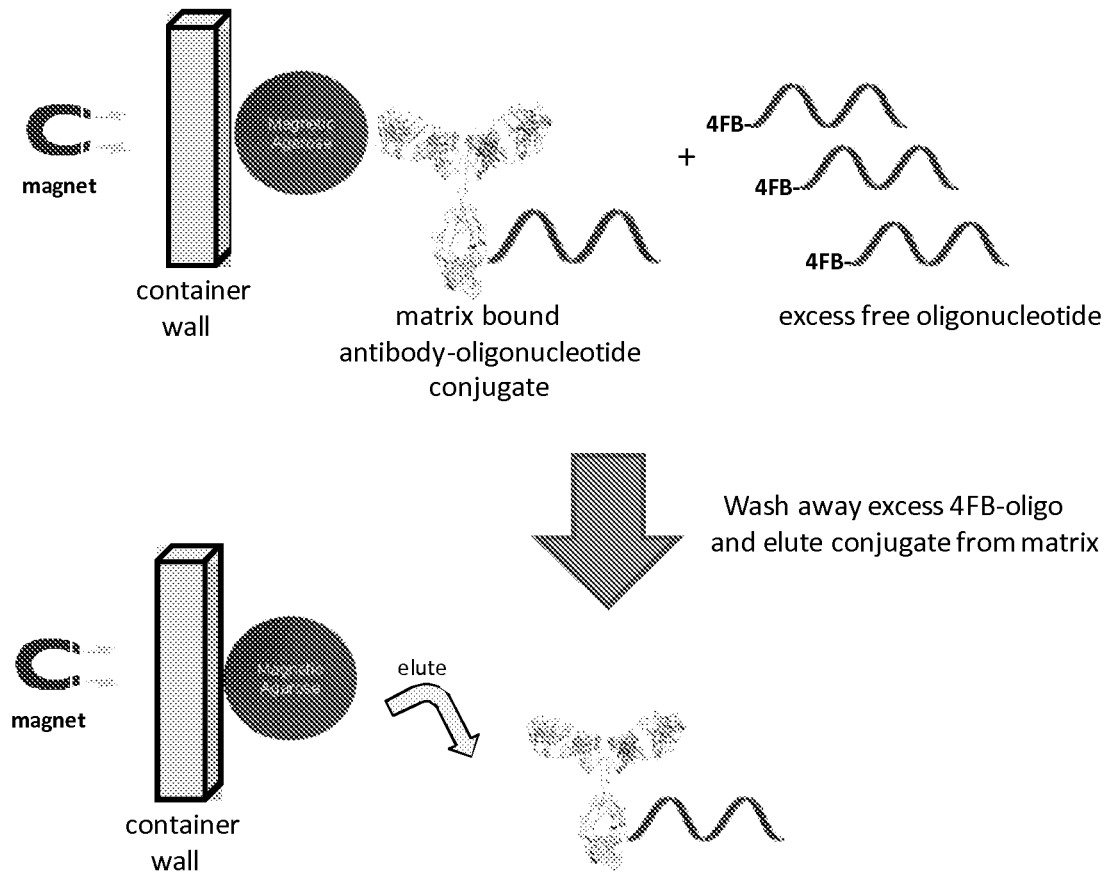
FIG. 10: Magnetic affinity purification of antibody-oligonucleotide conjugate, in accordance with certain embodiments.

In certain embodiments, the antibody-oligonucleotide conjugates may be purified as depicted in FIG. 10. For example, the conjugation reaction mixture, comprising antibody-oligonucleotide conjugates and, for example, excess modified oligonucleotide may be purified by binding the antibody-oligonucleotide conjugates to a column comprising agarose and metal ions immobilized within the stationary phase of the column (which may be called "magnetic agarose" or "magnetic affinity beads"). The prepared antibody-oligonucleotide conjugates may include moieties, such as a histidine rich region, that may bind to metal ions that are immobilized on the stationary phase of the column—which may now be separated from the excess modified oligonucleotide, which do not have functionality that may bind to the metal ions in a similar chelating fashion. Once the excess modified oligonucleotide has been washed by a series of elutions, the bound antibody-oligonucleotide conjugates may be released by eluting with a displacing agent, such as another chelating moiety, for example, EDTA.

Figure 11:
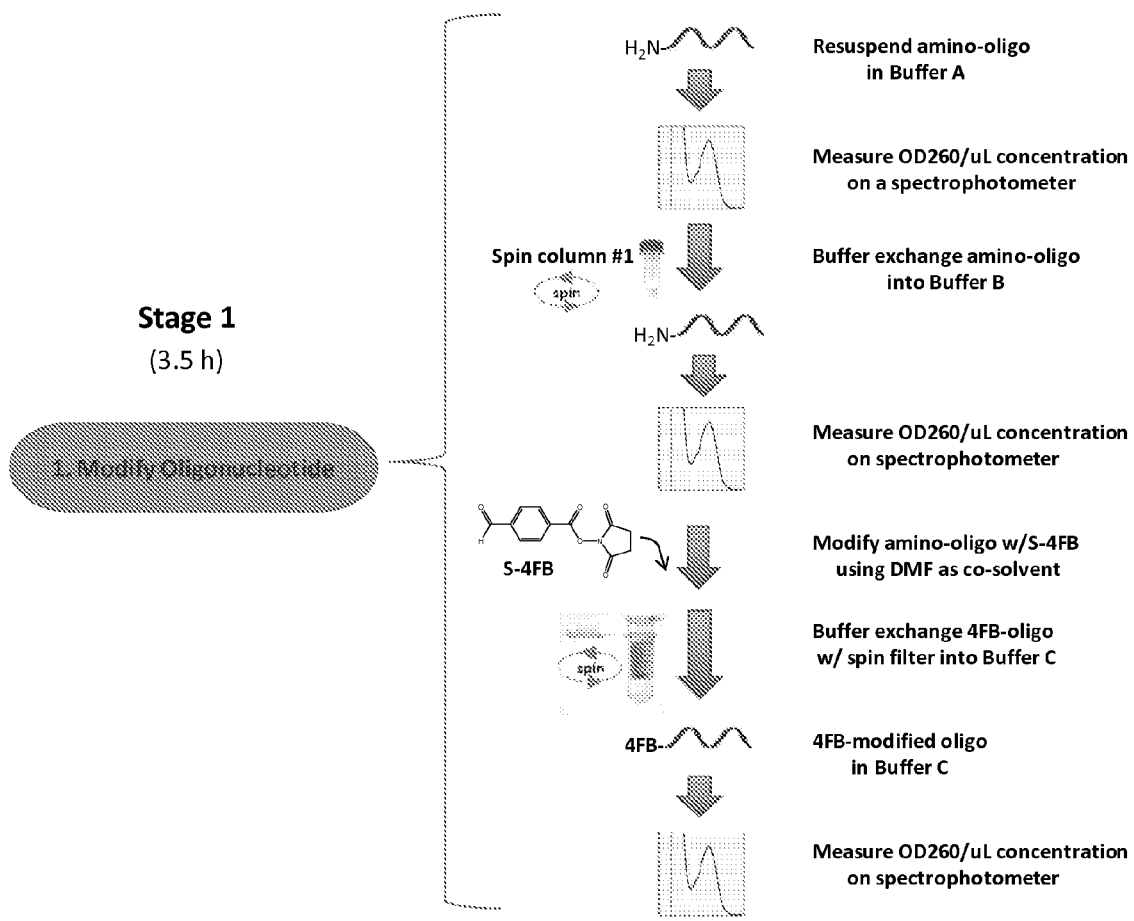
FIG. 11: Stage 1: Modification of the oligonucleotide to form a modified oligonucleotide, in accordance with certain embodiments.

In certain embodiments, the modified oligonucleotides may be prepared as depicted in FIG. 11. For example, in Stage 1, the modified oligonucleotides may be prepared by resuspending an amino-oligonucleotide in a buffer (Buffer A). The oligonucleotide concentration (OD260/μL) may be determined by spectrophotometer measurement. Once the concentration has been determined, the buffer solution may exchanged by sequential centrifuge spin down and resuspension of the resulting pellet in Buffer B to prepare for reacting with the modifying reagent, followed by measuring the oligonucleotide concentration (OD260/μL) in Buffer B by spectrophotometer measurement. Modification of the oligonucleotide may be conducted, for example, with S-4FB, using dimethylformamide (DMF) as a cosolvent. Once the reaction has completed, the reaction mixture may be spun down and the Buffer C exchanged into the system. Finally, the modified-oligonucleotide (4FB-modified oligonucleotide) concentration can be measured (OD260/μL) by spectrophotometer measurement, now in Buffer C.

In certain embodiments, the modified oligonucleotide may be prepared by solid phase synthesis. In certain embodiments, the solid phase synthesis may also include the direct incorporation of a linker during the solid phase oligonucleotide synthesis. In certain embodiments, the solid phase synthesis may also include the direct incorporation of a linker during the solid phase modified oligonucleotide synthesis.

Figure 12:
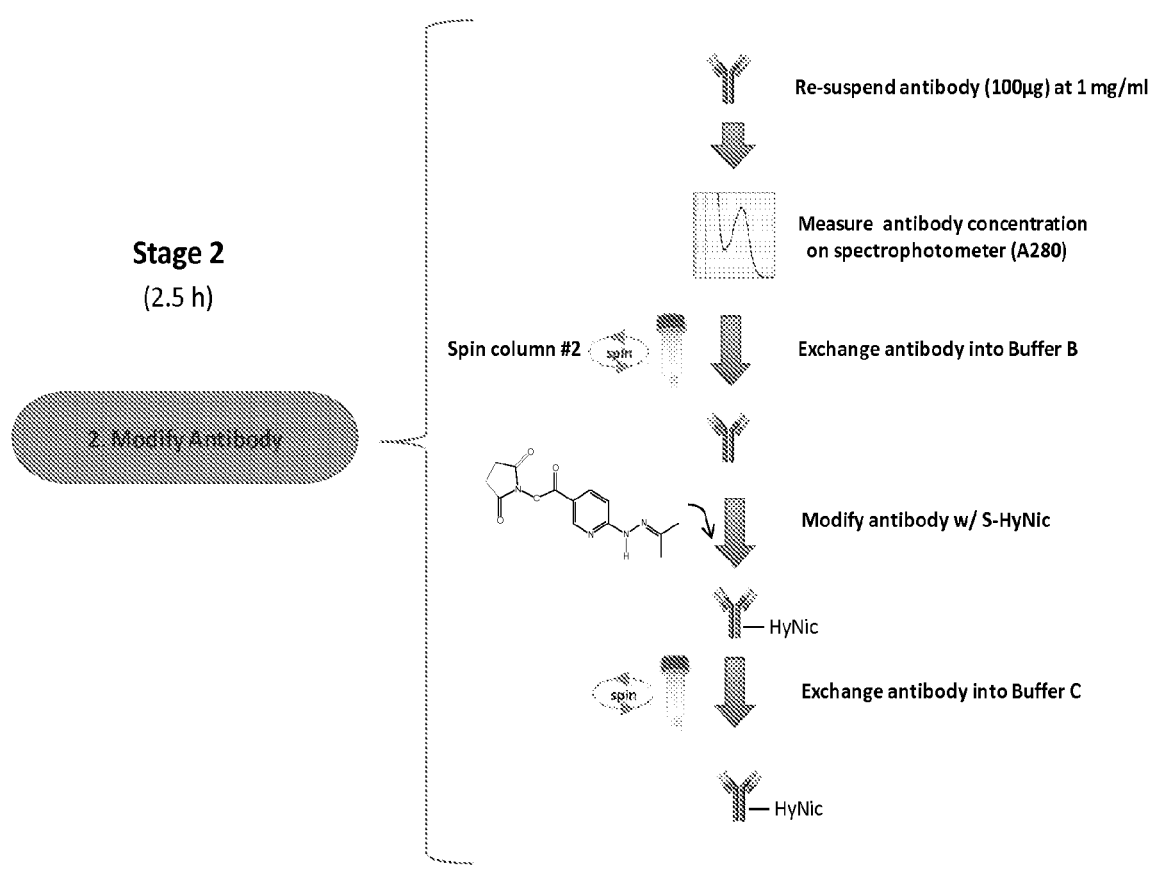
FIG. 12: Stage 2: Modification of the antibody to form a modified antibody, in accordance with certain embodiments.

In certain embodiments, the modified antibody may be prepared as depicted in FIG. 12. For example, in Stage 2, the modified antibodies may be prepared by resuspending the antibody in a buffer (for example 100 μg antibody at 1 mg/mL concentration). The antibody concentration (A280) may be determined by spectrophotometer measurement. Once the concentration has been determined, the buffer solution may exchanged by sequential centrifuge spin down and resuspension of the resulting pellet in Buffer B to prepare for reacting with the modifying reagent, for example, with S-HyNic. Once the reaction to modify the antibody has been completed, the reaction mixture may be spun down and the modified antibody, for example a S-HyNic-modified antibody, may be exchanged into Buffer C. Finally, the modified-antibody concentration, for example, the S-HyNic-modified antibody concentration, may be measured by a spectrophotometer measurement, now in Buffer C.

Figure 13:
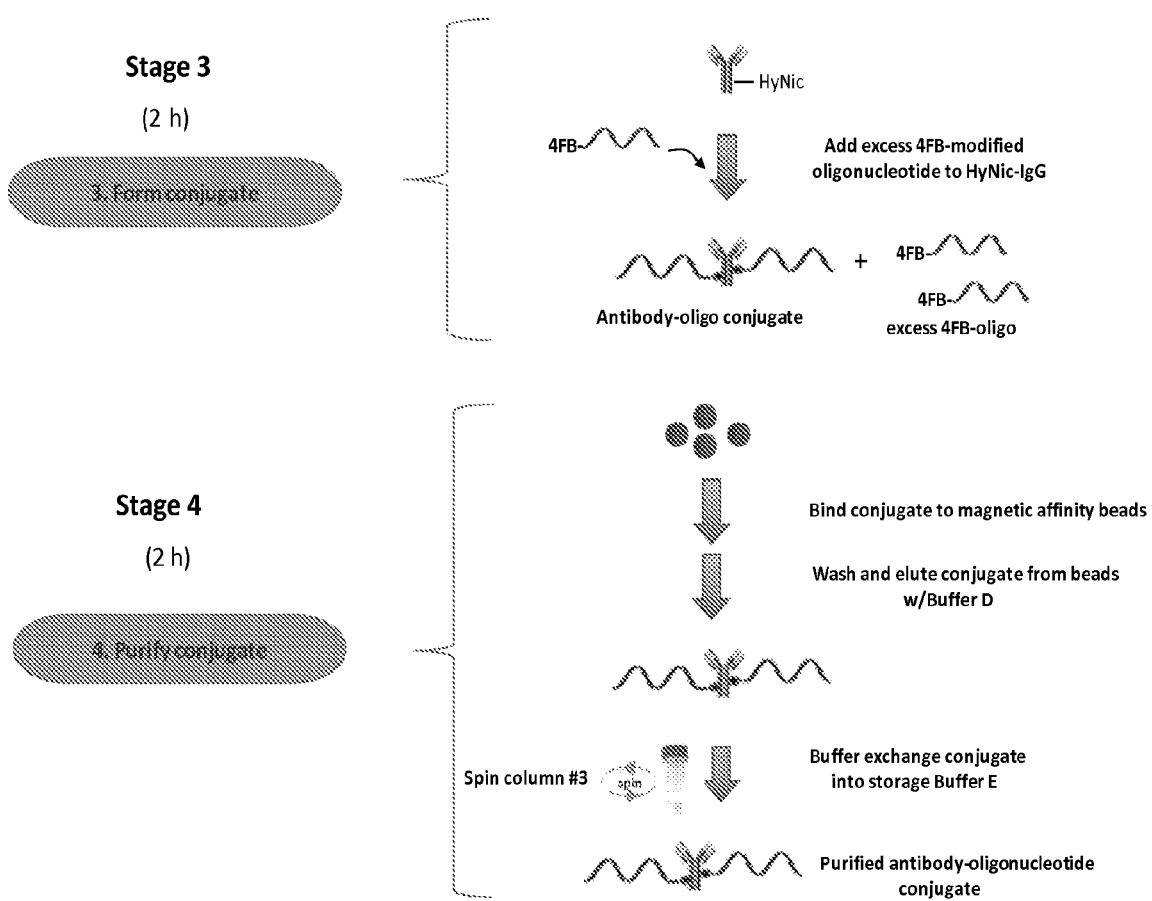
FIG. 13: Stage 3: Formation of the antibody-oligonucleotide conjugate. Stage 4: Purification of the antibody-oligonucleotide conjugate, in accordance with certain embodiments.

In certain embodiments, the conjugation of a modified antibody with a modified oligonucleotide may be conducted as depicted in Stage 3 in FIG. 13. For example, in Stage 3, the modified-antibody, for example a S-HyNic-modified antibody, may be reacted with an excess of the modified-oligonucleotide (4FB-modified oligonucleotide), to form antibody-oligonucleotide conjugates having at least one oligonucleotide conjugated to each modified-antibody, for example, at least two oligonucleotides conjugated to each modified-antibody. The reaction mixture will also have unreacted modified-oligonucleotide (4FB-modified oligonucleotide).

In certain embodiments, the purification and isolation of antibody-oligonucleotide conjugates may be conducted as depicted in Stage 4 in FIG. 13. For example, in Stage 4, the conjugation reaction mixture, comprising antibody-oligonucleotide conjugates and excess unreacted modified-oligonucleotides (4FB-modified oligonucleotide), may be placed in contact with "magnetic affinity beads," for example, beads having metal ions immobilized that are available to be bound selectively, by chelation, with the product antibody-oligonucleotide conjugates but not with the unreacted modified-oligonucleotides. Once the antibody-oligonucleotide conjugates have been bound to the magnetic affinity beads, the beads are washed to remove the remaining reaction components other than the bound antibody-oligonucleotide conjugates. The antibody-oligonucleotide conjugates are then released with a displacing agent, such as Buffer D, which then is buffered exchanged with Buffer E via sequential spin down and resuspension series, to provide purified antibody-oligonucleotide conjugates.

In certain embodiments, the protein-oligonucleotide conjugates may be prepared or purified, or both, as depicted in FIGS. 9, 10, 12 and 13, where a protein is modified rather than an antibody, and utilizing modified oligonucleotides as depicted in FIGS. 9, 10, 11 and 13.

The following provides a user-friendly manual, comprising some embodiments of the methods disclosed herein.

Solulink: Antibody-Oligonucleotide All-in-One™ Conjugation Kit (V.06.18.10) User Manual (Catalog No. A-9202-001)

An introduction to the Antibody-Oligonucleotide All-in-One™ Conjugation Kit.

An overview of the bioconjugation technology used to prepare antibody-oligonucleotide conjugates.

A list of required components and those to be provided by the user along with storage conditions.

This chapter contains the following sections: Product Description; All-in-One™ Conjugation Technology; All-in-One™ Conjugation Process; Starting Antibody Requirements; Starting Oligonucleotide Requirements; Kit Components; Materials Provided by the User; Component Storage Conditions.

A. Product Description: Each Antibody-Oligonucleotide All-in-One™ Conjugation Kit provides all the necessary components to generate one (1) antibody-oligonucleotide conjugate in just over 10 hours (~4 hr. hands on). The kit requires the user to supply the antibody (polyclonal or monoclonal, 100 µg) and one HPLC purified amino-modified oligonucleotide (10-40 OD260 units). Kit instructions are specifically designed for researchers with limited or no conjugation experience. A special conjugation calculator (located on a flash drive) is directly integrated with the protocol and avoids the need to perform numerical calculations throughout the procedure. Each kit yields between 20-60 µg of highly purified, ready-to-use antibody-oligonucleotide conjugate. Yield is dependent on both the specific antibody and oligo size. Final conjugate concentrations typically range from 0.1-0.3 mg/ml.

B. All-in-One™ Conjugation Technology: 1) Conjugation Chemistry. The Antibody-Oligonucleotide All-in-One™ Conjugation kit uses proprietary HydraLink™ chemistry to link an antibody to an oligonucleotide as illustrated in FIG. 9. The first stage of the process begins with the modification of a 3' or 5'-amino-modified oligonucleotide using an excess of a HydraLink™ linker called Sulfo-S-4FB. This reactive NHS-ester incorporates an aromatic aldehyde functional group, formylbenzamide (4FB) at the desired terminus of the oligonucleotide.

In a second stage of the process, a polyclonal or monoclonal antibody (100 µg) is modified using another HydraLink™ linker called S-HyNic. This NHS-ester reacts with lysine residues, incorporating HyNic functional groups (hydrazinonicotinamide) onto the antibody. In the third and final stage, the two modified biomolecules are mixed together in the presence of a reaction catalyst (i.e. aniline) to form the conjugate after which purification is carried out using a magnetic affinity solid phase.

Figure 14:
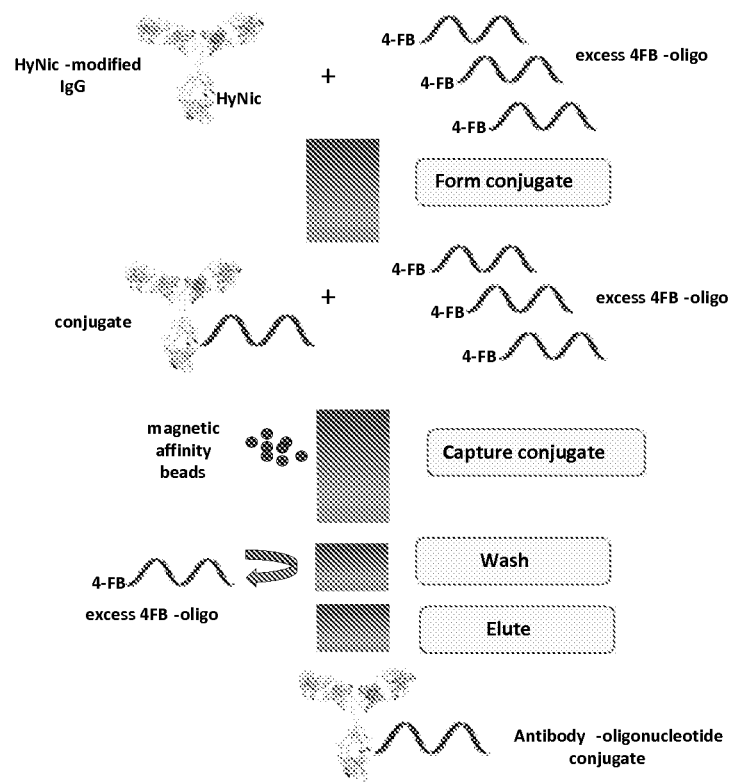
FIG. 14: All-in-One™ conjugate purification strategy.

2) Conjugate Purification. Antibody-oligonucleotide conjugates produced with the All-in-One™ kit are ready to be used in the most demanding and sensitive downstream applications. The kit delivers high purity conjugate virtually free of residual antibody or oligonucleotide (>98%). Reaction conditions are optimized to convert nearly 100% of the antibody into conjugate leaving only free, excess 4FB-oligo to be removed. Complete conversion of antibody to conjugate simplifies conjugate purification as illustrated in FIG. 14. Antibody-oligonucleotide conjugate is purified to near homogeneity by selectively binding the conjugate to a magnetic affinity matrix allowing excess 4FB-oligonucleotide to be washed away. Affinity bound conjugate is then gently eluted from the matrix and buffer exchanged into long term storage buffer. Antibody-oligonucleotide conjugates produced with the All-in-One™ are stable for up to 1 year when kept at 4° C. in storage buffer.

Figure 16:
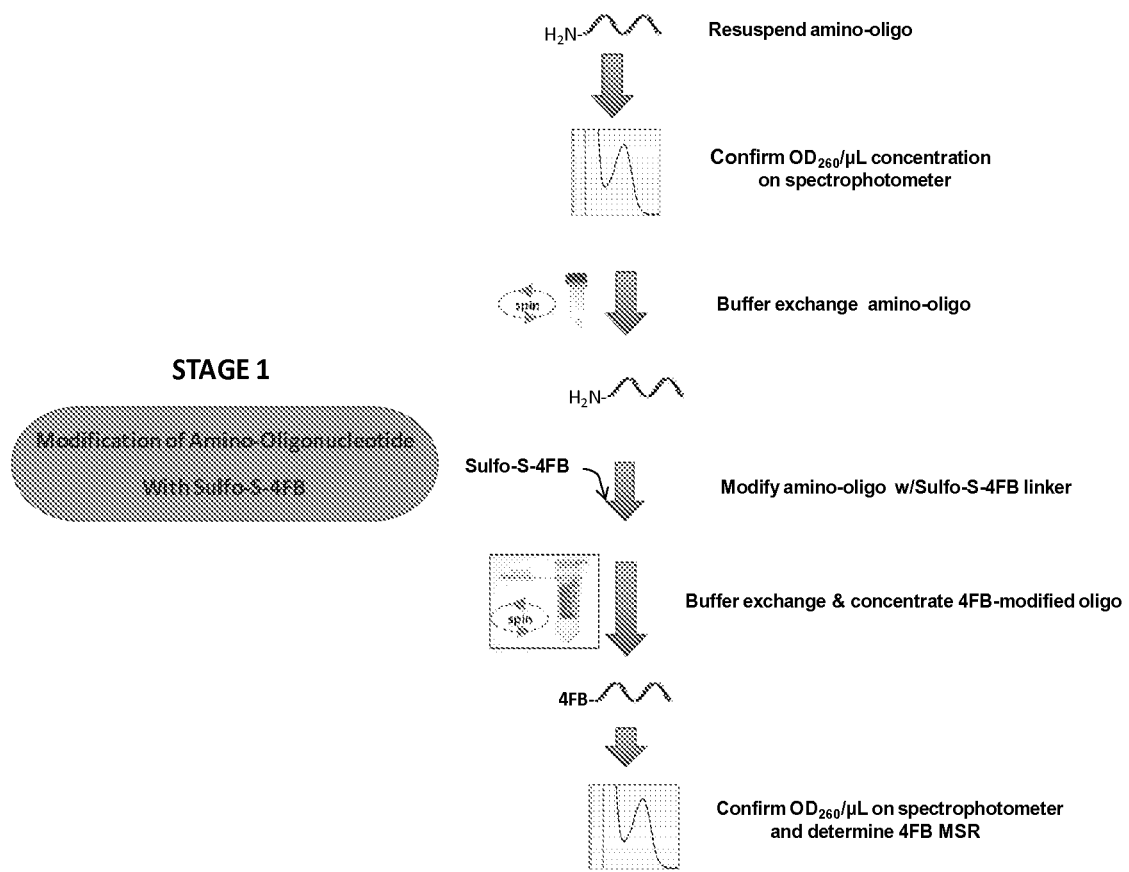
FIG. 16: Stage One (1) of the All-in-One™ conjugation process illustrates the modification of an amino-oligonucleotide using Sulfo-S-4FB linker.
Figure 17:
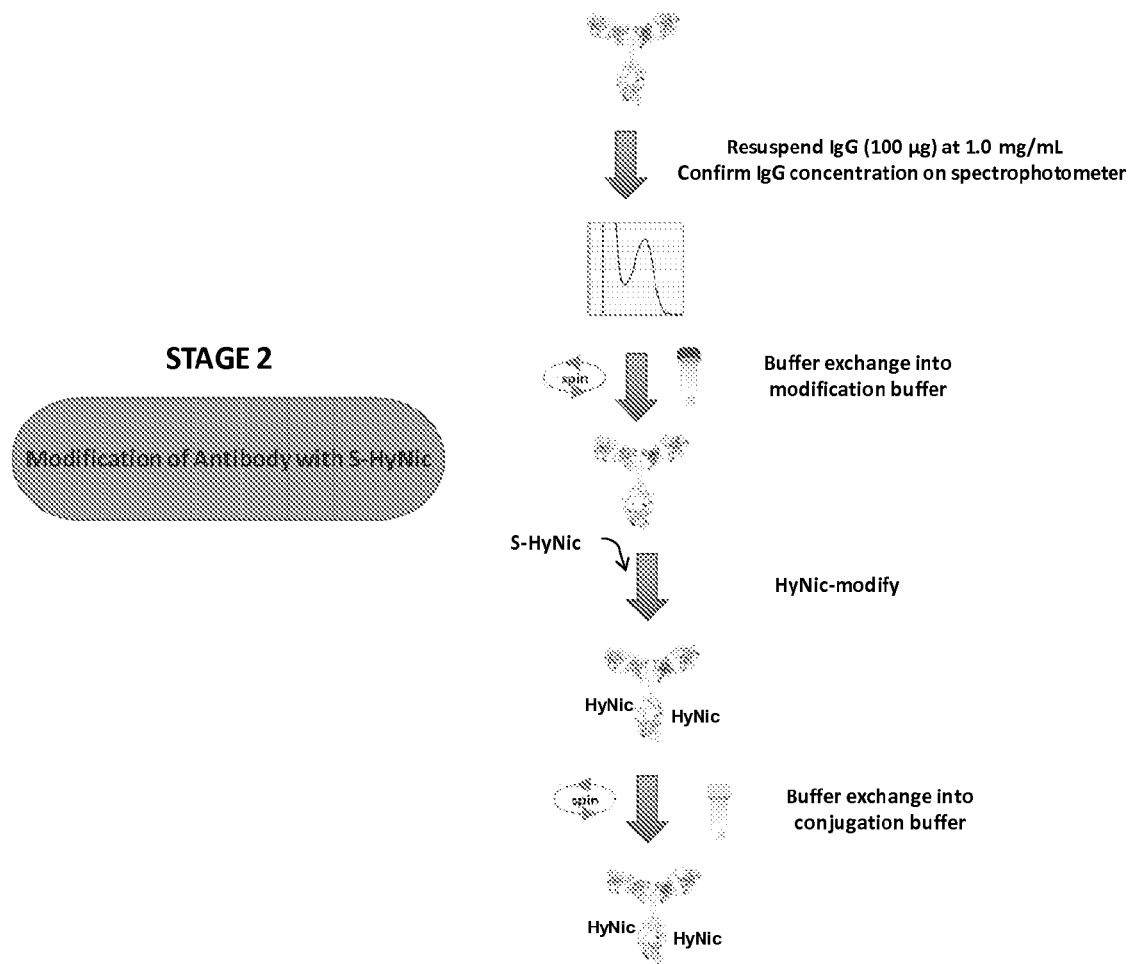
FIG. 17: Stage Two (2) of the All-in-One™ process illustrates the modification of IgG using S-HyNic linker.
Figure 18:
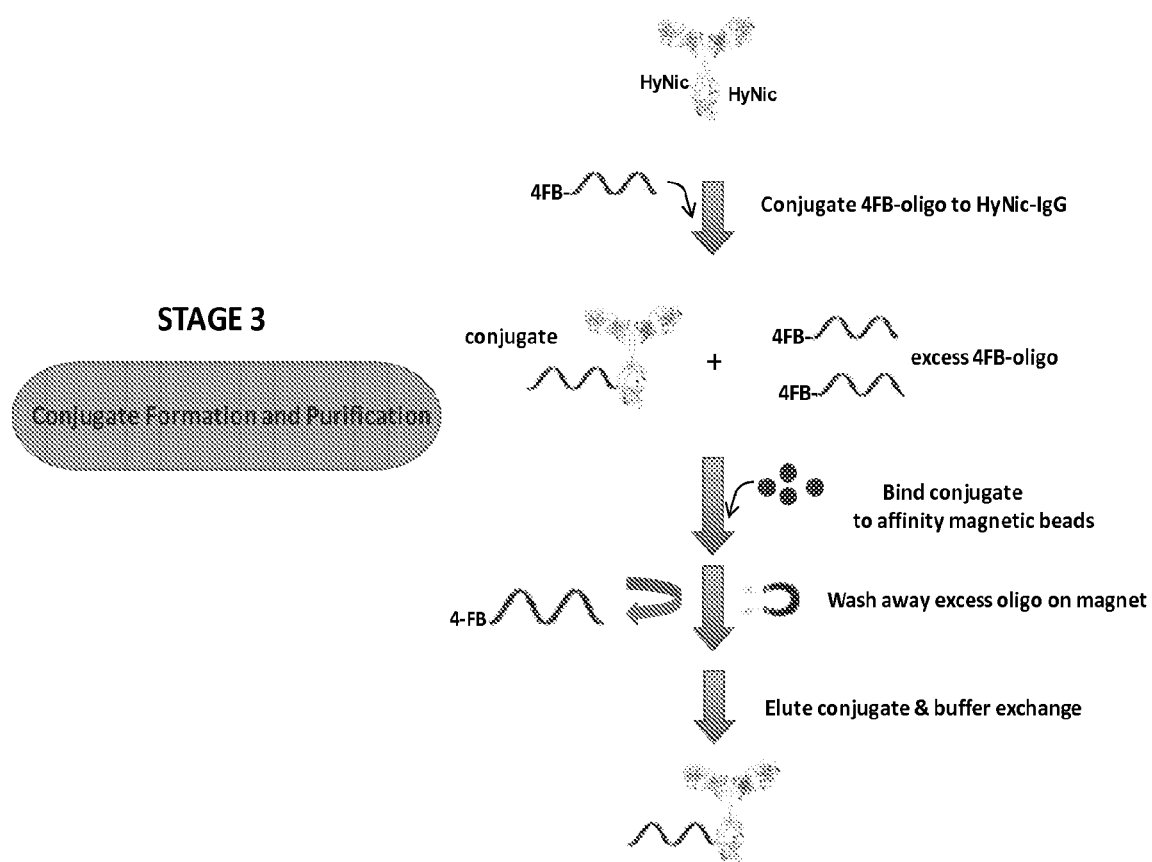
FIG. 18: Stage Three (3) of the All-in-One™ process illustrates both the formation and purification of the conjugate.
Figure 19:
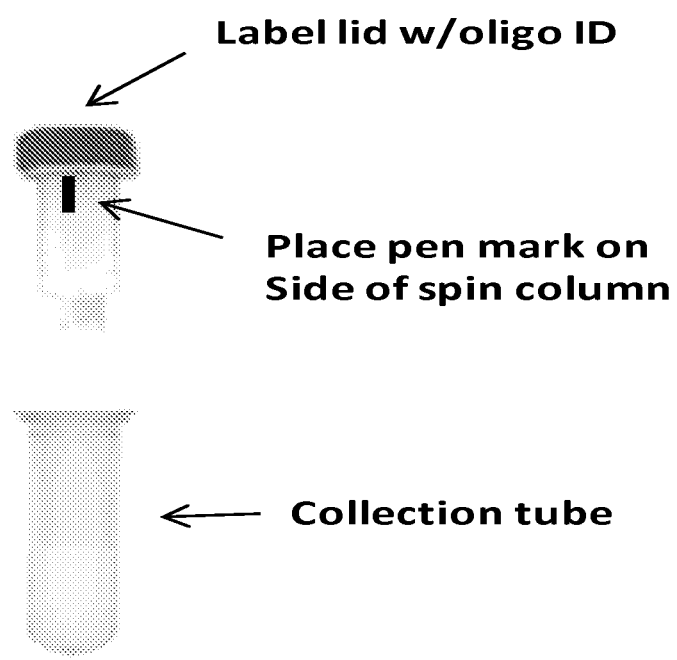
FIG. 19: Illustration showing how to prepare a buffer exchange spin column.
Figure 20:
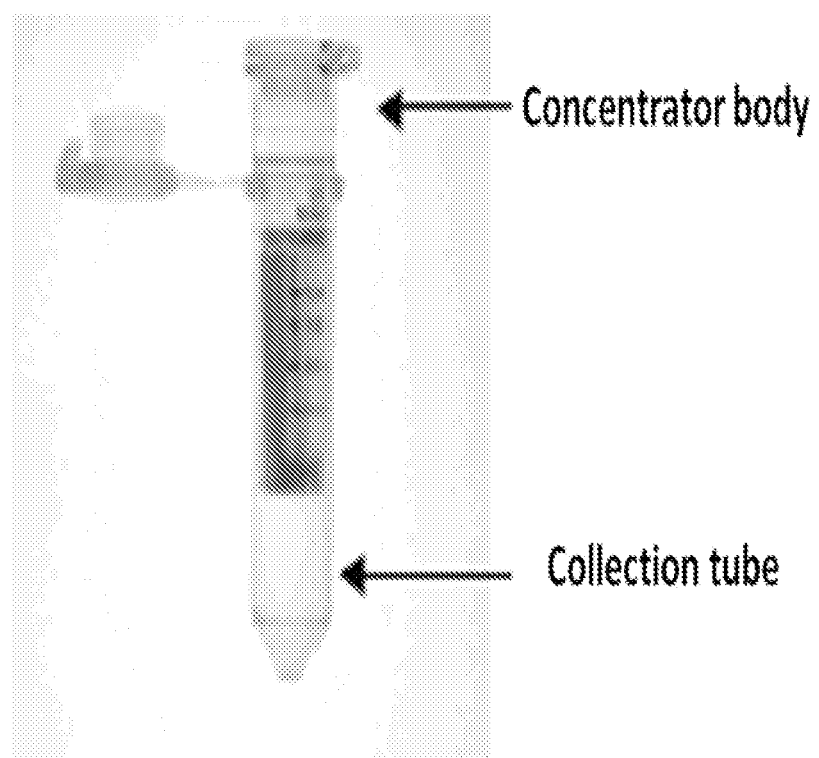
FIG. 20: Illustration showing a Pre-wet spin filter
Figure 21:
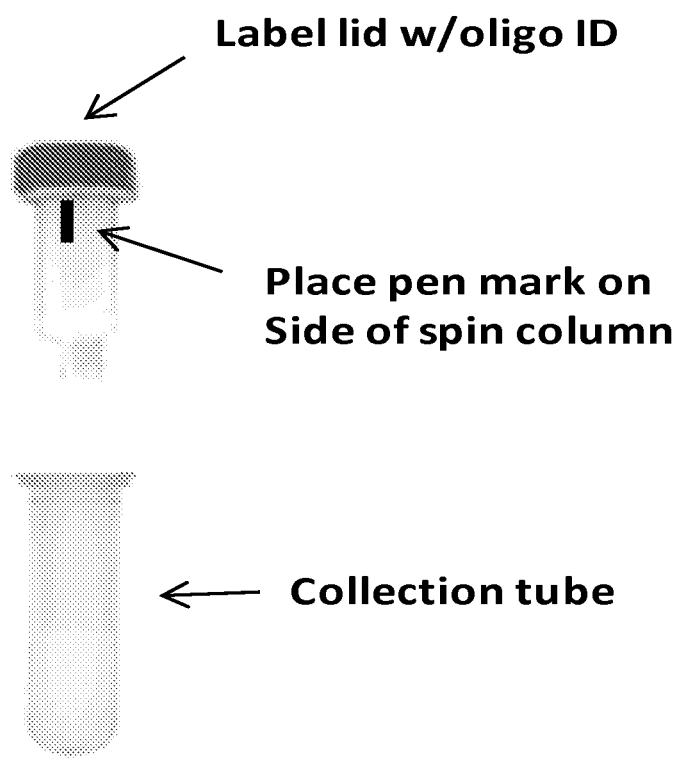
FIG. 21: Illustration showing labeling of spin column
Figure 22:
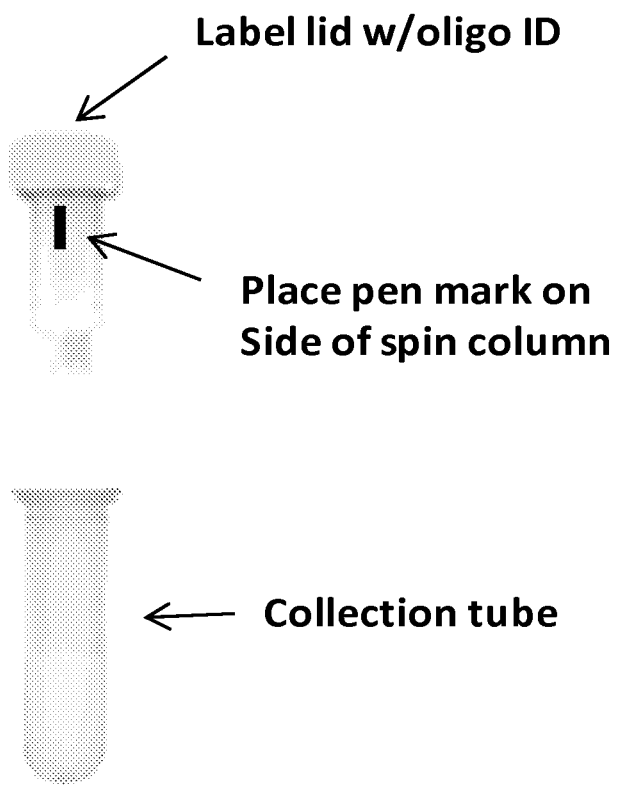
FIG. 22: Illustration showing labeling of spin column
Figure 23:
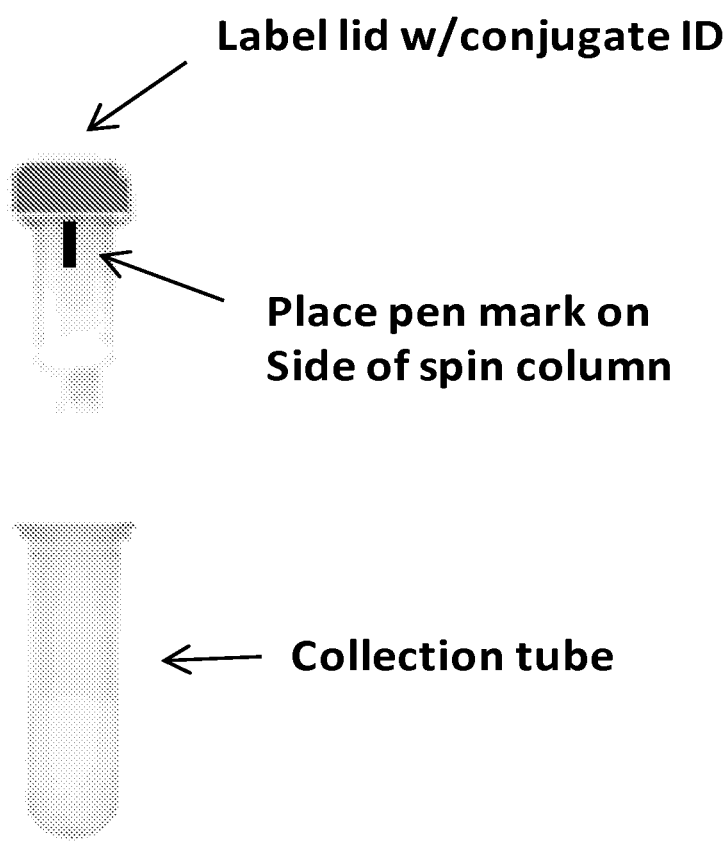
FIG. 23: Illustration showing labeling of spin column

C. All-in-One™ Conjugation Process. The three stages of the conjugation process as summarized below. Additional details are illustrated in FIGS. 16, 17, and 18.

D. Starting Antibody Requirements. The Antibody-Oligonucleotide All-in-One™ Conjugation Kit is designed to produce one (1) antibody-oligonucleotide conjugate starting with 100 µg of any mammalian antibody regardless of IgG subclass and one amino-modified oligonucleotide (10-40 OD260 units). The quality and quantity of both the starting antibody and oligonucleotide are critical to the success of the conjugation protocol. We recommend using only the highest quality antibodies and oligonucleotides from trusted sources and reputable vendors. This kit is not compatible with commercial antibody preparation containing added BSA or gelatin stabilizers. If present these additives must be removed before proceeding.

E. Starting Amino-Oligonucleotide Requirements. The Antibody-Oligonucleotide All-in-One™ kit is designed to conjugate any high purity 5' or 3' amino-modified oligonucleotide (20-60 nucleotides in length) to any monoclonal or polyclonal IgG-class antibody. The protocol requires a minimum quantity of 10 $OD_{260}$ and a maximum of 40 $OD_{260}$ units of HPLC purified amino-oligonucleotide. Solulink recommends that longer oligo sequences (e.g. >49-mer) be synthesized with a 5'-amino group and shorter oligos (<49-mer) with a 3'-amino group if the specific application permits. Oligonucleotides ≤49-mer can be either reverse phase (RP) or ion exchange purified (IEX) while longer oligos (>49-mer) can be IEX or double HPLC purified depending on the specific services offered by each vendor. Some vendors offer these purification options on a custom basis while others offer them as a standard service, albeit at additional cost.

Be advised that unpurified 3'-amino oligos contain a significant quantity of truncated failure sequences that lead to undesirable conjugation products while unpurified 5'-amino oligos contain up to 50% of A260 units in the form of shorter unmodified failure sequences that never form conjugate and thereby alter the stoichiometry of the conjugation reaction. For best results always use the highest quality, HPLC purified amino-oligonucleotide available.

Note: Please be advised that some oligo vendors will not HPLC purify amino-modified oligos or in some cases longer oligonucleotide sequences (modified or unmodified) except as a custom service. However some oligo suppliers do offer these services as a standard option. Solulink recommends that customers always use HPLC purified amino-oligonucleotides in this protocol. We recommend requesting a mass spectrum to confirm the final quality when available. The mass spectrum confirms percent full-length purity as well as molecular weight (unambiguous confirmation of amino group). As a general rule, we do not recommend using crude oligonucleotide preparations to make a conjugate. Use barrier pipette tips and good laboratory practices at all times to avoid potential contamination and/or cross-talk between different oligonucleotide sequences.

F. The Kit Components are shown in Table 1.

TABLE 1

| Component | Size | Storage |
|---|---|---|
| S-HyNic Linker | 1 × 100 µg | Keep desiccated at 4° C. |
| Sulfo-S-4FB Linker | 1 × 1.5 mg | Keep desiccated at 4° C. |
| Solution A | 10 mL | 4° C. |
| Solution B | 10 mL | 4° C. |
| Solution C | 10 mL | 4° C. |
| Solution D | 10 mL | 4° C. |
| Solution E | 0.25 mL | 4° C. |
| Spin Column (RedCap) | 2 × 0.5 mL | 4° C. |
| Spin Column (Yellow Cap) | 1 × 0.5 mL | 4° C. |
| Spin Column (BlueCap) | 2 × 0.5 mL | 4° C. |
| DMF | 1 × 1.0 mL | 4° C. |
| Conjugate Quench | 1 mL | 4° C. |

TABLE 1-continued

| Component | Size | Storage |
| --- | --- | --- |
| Reagent | | |
| 2-HP Reagent | 1 mL | 4° C. |
| Affinity Magnetic Beads | 1 × 75 µL | 4° C. |
| Oligo Spin Filter | 1 | Room Temperature (18-25° C.) |
| Collection Tubes | 10 | Room Temperature (18-25° C.) |
| Flash Drive | 1 | Room Temperature (18-25° C.) |

G. Materials to be Provided by the User. Variable high speed microcentrifuge (e.g. Eppendorf 5415D or equivalent); Magnetic single 1.5 ml tube stand (e.g. Ambion #AM10026); UV-VIS Scanning Spectrophotometer or ND-1000 Nano-Drop™; UV-VIS scanning plate reader (Bradford Assay) (Optional); Micro-volume quartz cuvette (50-100 µL) if a NanoDrop™ is not available; 1.5 mL microfuge tubes; Bradford protein assay reagents (Bio-Rad, #500-0006); Bovine IgG concentration standards (Pierce, #23212); Calibrated pipettes (P-2, P-10, P-200 and P-1000) and barrier tips; Table-Top Centrifuge (holds 50 mL conical tubes) (Optional).

H. The Component Storage Conditions are shown in Table 2.

TABLE 2

| Component | Storage |
| --- | --- |
| Kit | 2-8° C. |
| S-HyNic Reagent - Desiccated | 2-8° C. |
| Sulfo-S-4FB Reagent - Desiccated | 2-8° C. |
| All other components and buffers | 2-8° C. |
| HyNic-modified antibody | 2-8° C. |
| Antibody-oligonucleotide conjugate | 2-8° C. |
| 4FB-modified oligonucleotide | −20° C. |
| Flash Drive | Ambient |

The conjugation protocol is a three stage process (~10.5 hours in duration) where each step takes several hours to complete. If desirable, the end-user can complete Stage 1 on the first day (~4 hr) then proceed with Stages 2 and 3 on day two (6.5 hr). Keep in mind that we do not recommend stopping the procedure after Stage 2. The only convenient stopping point throughout the entire protocol is immediately after Stage 1 so we recommend that you schedule and plan your time accordingly. Total hands-on is approximately 4 hrs.

If the starting amino-oligo is in dry pellet form: If the amino-oligo to be modified with Sulfo-S-4FB is in dry pellet form and contains a minimum of 10 OD260 units and no more than 40 OD260 units, proceed to Stage 1. If more than 40 OD260 units are provided by the vendor in a dry pellet form do not make adjustments to the OD260 units at this time and proceed to Stage 1.

If the starting amino-oligo is in a liquid form: If the amino-oligonucleotide to be modified with Sulfo-S-4FB is already in liquid form and its concentration is known (units of OD260/µL), then transfer to another tube a volume equivalent to a minimum of 10 OD260 units and no more than 40 OD260 units and concentrate into a dry pellet form using a vacuum concentrator (e.g. SpeedVac™ from Savant Instruments) then proceed to Stage 1.

If the initial amino-oligo to be modified is already in liquid form and its concentration is unknown (units of OD260/µL), then measure its concentration as described in this Chapter (Section C). Transfer into another tube a volume equivalent to a minimum of 10 OD260 units and no more than 40 OD260 units and concentrate into a dry pellet form using a vacuum concentrator then proceed to Stage 1.

Stage 1: Modification of Amino-Oligonucleotide with Sulfo-S-4FB

A. Enter Amino-Oligo Information into Conjugation Calculator:

1. Enter the following amino-oligo parameters directly from the Oligo vendor's Certificate of Analysis into the Conjugation Calculator (Section A, green cells):
    a) Oligonucleotide name as listed on the Certificate of Analysis;
    b) Total OD260 units as listed on the Certificate of Analysis;
    c) Oligonucleotide molar extinction coefficient (liter cm$^{-1}$ mol$^{-1}$) as listed on the Certificate of Analysis;
    d) Oligonucleotide molecular weight (Daltons) as listed on the Certificate of Analysis;
    e) Nanomoles of amino-oligonucleotide as listed by vendor on the Certificate of Analysis.

Enter the total OD260 units and the number of nanomoles provided by the vendor on the Certificate of Analysis even if only a portion of the total OD260 units provided are going to be modified. The calculator requires the total values provided on the Certificate of Analysis to determine the number of nanomoles/OD260.

If the original Certificate of Analysis is not available for whatever reason, the required information can still be generated by pasting and analyzing the known oligo sequence (including modifications) on Integrated DNA Technologies website using their commercial Oligo Analyzer (see link below). In these cases, since the total OD260 units and nanomoles provided by the vendor on their original Certificate of Analysis is no longer available, you must enter the number of OD260 units actually being modified as well as the number of nanomoles represented by that OD260 units into the Conjugation Calculator.

Failure to enter all the required information into the conjugation calculator as stated on the vendor's Certificate of Analysis will disrupt and void subsequent calculator functions. Always save the calculator spreadsheet after data entry.

B. Resuspend Amino-Oligo

1. Resuspend the amino-oligo provided (e.g. minimum of 10 OD260 units) into 100 µL Solution A. Pipette the solution up and down 30 times using a P-200 pipette (barrier tip) to completely resuspend the oligo pellet. Also rinse the wall of the container with pipette action to insure that any and all oligo pellet material has been resuspended completely.

2. If more than 40 OD260 units are resuspended, transfer a volume equivalent to 40 OD260 units into another tube and adjust the final volume to 100 µL with Solution A. Store the remaining unused portion of the resuspended amino-oligonucleotide at −20° C.

3. Vortex the oligo solution for 60 seconds then centrifuge the amino-oligonucleotide for 10 seconds at 1,000×g to collect the full liquid contents at the bottom of the vial. Proceed to measure the oligo concentration.

C. Measure Amino-Oligo Concentration on a Spectrophotometer: The amino-oligo concentration can measured either on a conventional or micro-volume UV-VIS scanning spectrophotometer (e.g. NanoDrop™ ND-1000). When using a conventional spectrophotometer a quartz micro-cuvette (50-100 µL) is required. Follow the corresponding instructions for each type of spectrophotometer as summarized below.

Micro-Volume Spectrophotometer (e.g. NanoDrop™ ND-1000)

Determine the concentration (OD260/µL) of the resuspended amino-oligo on a NanoDrop™ as follows (remember to use barrier tips):

a) Prepare a 1:250 dilution of the dissolved amino-oligo by transferring 1 µL with a calibrated P-2 pipette into 249 µL molecular grade H$_2$O.

b) Select the "Nucleic Acid" menu option on the Nano-Drop™ and initialize the instrument using molecular grade water.

c) Clean the sample pedestal and blank the instrument with 2 µL molecular grade H$_2$O. Check the baseline and reblank if necessary to insure that it is flat.

d) Measure the A260 of the 1:250 amino-oligo as displayed in the 10 mm path length window. Record the A260 value.

Enter the recorded A260 into the Conjugation Calculator (Section B, green cell). The calculator determines the A260/µL as well as the total OD260 oligo units available for conjugation (Section B, yellow cells). A minimum of 10 OD260 and a maximum of 40 OD260 units are required.

Important—If less than 10 OD260 units are recovered after resuspension obtain additional amino-oligo. If greater than 40 OD260 are resuspended transfer an aliquot equivalent to 40 OD260 units into another tube and bring the final volume to 100 µL with Solution A, then proceed with the protocol.

Conventional UV-VIS Spectrophotometer

Determine the concentration (OD260/µL) of the resuspended amino-oligo using a quartz micro-cuvette (50-100 µL, 1-cm path length) and a spectrophotometer as follows (remember to use barrier tips).

a) In a 1.5 mL tube prepare a 1:250 dilution of the resuspended amino-oligo by transferring 1 µL with a calibrated P-2 pipette into 249 µL molecular grade H$_2$O.

b) Blank the spectrophotometer at 260 nm using molecular grade H$_2$O.

c) Measure the A260 of the 1:250 amino-oligo. Record the A260 value.

Enter the recorded A260 into the Conjugation Calculator (Section B, green cell). The calculator determines the A260/µL as well as the total OD260 oligo units available for conjugation (Section B, yellow cells). A minimum of 10 OD260 and a maximum of 40 OD260 units are required.

Important—If less than 10 OD260 units are recovered after resuspension obtain additional amino-oligo. If greater than 40 OD260 are resuspended transfer an aliquot equivalent to 40 OD260 units into another tube and bring the final volume to 100 µL with Solution A, then proceed with the protocol.

D. Buffer Exchange Amino-Oligo

1. Prepare a buffer exchange spin column (red cap) by twisting off the bottom closure and loosening the red cap (do not remove the cap). Place the spin column into a collection tube (provided).

2. Mark the top of the spin column (red cap) using an indelible pen to identify the oligo sequence. Using the same marker pen place a single vertical mark anywhere on the side of the spin column as illustrated below.

3. Place the spin column assembly into the centrifuge and balance appropriately with an opposing balance tube. Orient the vertical mark on the side of the spin column by aiming it outward and away from the center of the rotor.

4. Centrifuge at 1,500×g for 1 minute. Discard the flow through from the bottom of the collection tube. The column matrix will appear white in color. Place the column back into a new empty collection tube (provided).

5. Apply the dissolved amino-oligo (10-40 OD260 units per 100 µL) in Solution A to the top of the dry resin bed. Place the spin column into the empty collection tube. Loosely recap and properly orient the spin column in the centrifuge. Centrifuge at 1,500×g for 2 min.

Important—Rotor speed must be set to 1500×g (RCF) and not 1500×rpm (RPM). The volume of oligo recovered in the collection tube should always be approximately the same volume that is loaded on the spin column. For example, when 100 µL of amino-oligo is loaded, 100±10 µL should be recovered. If the recovered volume is low it is likely that rotor speed is not calibrated. If this happens, re-centrifuge the spin column at 1,500×g speed for an additional minute to recover any trapped solution the spin column.

6. Measure the recovered volume (µL) of amino-oligo at the bottom of the collection tube using a P-200 pipette and transfer it to a new 1.5 mL tube.

Note—Yield in A260 units through a spin column is generally >90% for amino-oligos ranging in size from 35-60 bases. Recovery yields from smaller oligos (e.g. 20-mers) are somewhat lower (e.g. 75%) due to the size exclusion limit of the spin column matrix. Never spin oligos smaller than 20-mers through a spin column to avoid oligo loss.

7. Label the tube with the corresponding oligo ID and volume (µL) recovered. The amino-oligo is now ready for 4FB modification.

E. Dissolve Sulfo-S-4FB Reagent

Add 25 µL DMF to the vial of Sulfo-S-4FB reagent; vortex for 30 seconds to resuspend. Pipette the DMF solution up and down if necessary to fully resuspend the material adhered to the wall of the vial.

F. Modify Amino-Oligo with Sulfo-S-4FB Reagent

1. Enter the volume of amino-oligo to be modified with Sulfo-S-4FB into the Conjugation Calculator (Section C, green cell).

2. Add the indicated volume (µL) of dissolved Sulfo-S-4FB reagent as displayed in the Conjugation Calculator (Section C, yellow cell) to the amino-oligo; vortex to mix. Centrifuge at 1000×g for 10 seconds to collect the entire liquid contents at the bottom of the tube.

3. Incubate at room temperature for 2 hours to modify the oligo.

G. Buffer Exchange and Concentrate 4FB-Oligo

Five minutes prior to the end of the 4FB/oligo modification reaction, pre-wet an Oligo Spin Filter as described in this section.

Pre-Wet Spin Filter

1. Open the lid of an assembled filter unit; pre-wet the filter membrane inside the concentrator body (see image below) by adding 500 µL Solution C to the filter membrane.

2. Pipette the solution up and down using a P-1000 pipette several times without touching or damaging the filter membrane.

3. Open the lid to the filter unit and with gloved hands remove the concentrator body from the collection tube and with a rapid inverted flick of the wrist discard the entire volume of Solution C from the concentrator body into a suitable waste receptacle. Place the empty concentrator body back into the collection tube.

Buffer Exchange 4FB-Oligo

1. Transfer the completed Sulfo-S-4FB/amino-oligo modification reaction into the empty concentrator body (~100-125 µL).

2. Add 400 µL Solution C to the concentrator body to bring the total volume to approximately 500 µL.

3. Using a P-1000 pipette, mix the solution in the concentrator body up and down with pipette action ~10-15 times without touching or damaging the filter surface.

4. Close the lid and mark the filter unit with an identifying name or ID.

5. Orient the oligo spin filter in the centrifuge so the volume calibration numbers face toward the center of the rotor. Remember to use an appropriate balance tube opposite the oligo spin filter unit.

6. Centrifuge at 15,000× g for 12 min. After centrifugation, the volume in the concentrator body will generally be between 25 and 50 µL; some translucent color may be associated the concentrated solution (e.g. light brown).

Note—We recommend as a precautionary measure, after the first spin that you may wish to retain the flow-through from the bottom of the collection tube just in case the filter membrane is defective or has been damaged.

7. Repeat steps—2 through 6 four (4) additional times to completely buffer exchange and concentrate the 4FB-oligo. Do not skip any of the spin steps.

8. Important—Although five spin cycles are time consuming and tedious (total time~1 h) proper execution of this step is critical to the success of the conjugation reaction by removing excess Sulfo-S-4FB.

9. After the final spin, check the volume in the concentrator unit. If the final volume is less than 25 µL simply adjust the volume to 25 µL by adding a small aliquot of Solution C. If the final volume is greater than 25 µL, continue to centrifuge the spin filter for a few more minutes until the volume reaches 25 µL.

10. Open the lid of the filter unit and using a P-20 pipette carefully pipette the solution up and down 15 times to fully resuspend the 4FB-oligo.

11. Using the same pipette, rinse the filter's surface 5 or 6 times with the oligo solution by repeatedly pipetting the 4FB-oligo solution over the entire surface of the filter. This rinsing process insures that any filter bound 4FB-oligo is brought back into solution.

12. Close the lid of the filter unit and insert it back into the collection tube. Briefly centrifuge for 10 seconds at 1,000×g to collect the full 25 µL of 4FB-oligo back at the bottom of the concentrator unit.

Leave the 4FB-modified oligo inside the concentrator unit at this time and proceed to measure the 4FB-oligo concentration on a spectrophotometer.

Note—If the filter is not sufficiently or properly rinsed some 4FB-oligo can remain bound to the filter surface. Leave the 4FB-oligo solution in the filter unit until the 4FB-oligo concentration (OD260/µL) is confirmed on the spectrophotometer.

H. Measure 4FB-Oligo Concentration

Measure the concentration of 4FB-modified oligonucleotide (OD260/µL) within the filter concentrator body using a micro-volume UV-VIS scanning spectrophotometer (e.g. NanoDrop™ ND-1000) or a conventional spectrophotometer. When using a conventional spectrophotometer a quartz micro-cuvette (50-100 µL, 1-cm path length) is required. Use the instructions below depending on the specific type of spectrophotometer available to you (NanoDrop™ or Conventional).

Concentration Using a Micro-Volume NanoDrop™ Spectrophotometer

1. Prepare a 1:1000 dilution of the 4FB-modified oligo by transferring 1 µL (calibrated P-2 pipette) from inside the spin filter concentrator body to a 1.5 mL tube containing 999 µL molecular grade $H_2O$. Label the tube with the appropriate oligo ID.

2. Select the "Nucleic Acid" menu option on the Nano-Drop™ and initialize the instrument.

3. Clean the sample pedestal and blank the instrument with molecular grade $H_2O$. Confirm a flat baseline by clicking on the "Re-blank" icon and reblank if necessary. Clean the sample pedestal dry.

4. Measure the A260 of a 2 µL aliquot of the 1:1000 4FB-oligo dilution as displayed in the 10 mm path length window.

5. Enter the resulting A260 into Conjugation Calculator (Section D, green cell). The calculator will then display the concentration of the 4FB-oligo in units of A260/µL (Section D, $1^{st}$ yellow cell). If the calculator displays 'YES' (Section D, $2^{nd}$ yellow cell) then proceed to step 6 below. If the calculator displays "FALSE" (Section D, $2^{nd}$ yellow cell) proceed to step 7 below.

6. When the measured 4FB-oligo concentration is in the required range (0.3 to 0.6 OD260/µL), proceed to measure the oligo 4FB Molar Substitution Ratio as described in Section I of this protocol. Leave the 4FB-Oligo solution in the concentrator unit until after Section I is complete.

7. If the 4FB-oligo concentration displayed is greater than 0.6 OD260/µL, dilute the 4FB-oligo in the filter unit by adding the indicated volume of Solution C (µL) from the Conjugation Calculator (Section D, $3^{rd}$ yellow cell) to obtain 0.6 OD260/µL. Then re-enter the adjusted value (0.6 OD260/µL) into the Conjugation Calculator (Section D, green cell). Once the 4FB-oligo is adjusted to 0.6 OD260/µL, proceed to measure the oligo 4FB Molar Substitution Ratio as described in Section I of this protocol. Leave the 4FB-Oligo solution in the concentrator unit until after Section I is complete.

Important—If the oligo concentration is less than 0.3 OD260/µL at this juncture, re-concentrate the 4FB-oligo in the concentrator unit with additional centrifugation time at 15,000×g until a volume of ~15-20 µL is reached and then re-confirm OD260/µL. When the required 4FB-oligo concentration is obtained, re-enter the measured value into the Conjugation Calculator (Section D, green cell) and proceed to Section I of this protocol. Leave the 4FB-Oligo solution in the concentrator unit until after Section I is complete.

Concentration Using a Conventional UV-VIS Spectrophotometer

1. Prepare a 1:1000 dilution of the 4FB-modified oligo by transferring 1 µL (calibrated P-2 pipette) from inside the spin filter concentrator body to a tube containing 999 µL molecular grade $H_2O$. Label the tube with the appropriate 4FB-oligo ID.

2. Using a quartz micro-cuvette, blank the spectrophotometer at 260 nm with molecular grade $H_2O$. Discard the blank solution from the cuvette.

3. Measure the A260 of 1:1000 oligo dilution.

4. Enter the resulting A260 into the Conjugation Calculator (Section D, green cell). The calculator will then display the concentration of the 4FB-oligo in units of A260/µL Conjugation Calculator (Section D, $1^{st}$ yellow cell). If the calculator displays 'YES' (Section D, $2^{nd}$ yellow cell) then proceed to step 5 below. If the calculator displays "FALSE" (Section D, $2^{nd}$ yellow cell) proceed to step 6 below.

5. When the measured 4FB-oligo concentration is in the required range (0.3 to 0.6 OD260/µL), proceed to measure the oligo 4FB Molar Substitution Ratio as described in Section I of this protocol. Leave the 4FB-Oligo solution in the concentrator unit until after Section I is complete.

6. If the 4FB-oligo concentration displayed is greater than 0.6 OD260/µL, dilute the 4FB-oligo in the concentrator unit by adding the indicated volume of Solution C (µL) Conjugation Calculator (Section D, $3^{rd}$ yellow cell) to obtain 0.6 OD260/µL then re-enter this adjusted value into the Conjugation Calculator (Section D, green cell). Once the 4FB-oligo is adjusted to 0.6 OD260/μL, proceed to measure the oligo 4FB Molar Substitution Ratio as described in Section I of this protocol. Leave the 4FB-Oligo solution in the concentrator unit until after Section I is complete.

Important—If the oligo concentration is less than 0.3 OD260/μL at this juncture, re-concentrate the 4FB-oligo in the concentrator unit with additional centrifugation time at 15,000×g until a volume of ~15-20 μL is reached and re-confirm the OD260/μL. When the required 4FB-oligo concentration is obtained, re-enter the measured value into the Conjugation Calculator (Section D, green cell) and proceed to Section I of this protocol. Leave the concentration adjusted 4FB-Oligo solution in the concentrator unit until after Section I is complete.

I. Measure and Quantify 4FB Molar Substitution Ratio

The following 4FB Molar Substitution Assay quantifies the amount of 4FB attached to the oligonucleotide. The assay is performed by reaction of an aliquot (2 μL) of the 4FB-oligo solution (0.3 to 0.6 OD260/μL) with 2-HP reagent at 37° C. for 30 minutes after which the A260 and A360 of the sample is measured on a spectrophotometer. This assay insures that the oligo is both 4FB-modified and properly buffer exchanged (removal of excess Sulfo-S-4FB). Use the appropriate instructions below depending on the specific type of spectrophotometer available to you (e.g. NanoDrop™ or Conventional).

4FB Molar Substitution Assay (NanoDrop™)

1. Prepare a 2-HP blank solution by adding 2 μL Solution C to 18 μL 2-HP Reagent; label '2-HP Blank'.

2. Prepare a 4FB-oligo sample by adding 2 μL 4FB-modified oligo (0.3-0.6 OD260/μL) to 18 μL 2-HP reagent; label '4FB-Oligo'.

3. Incubate 2-HP blank and 4FB-Oligo reactions at 37° C. for 30 minutes.

4. Launch the NanoDrop™ software and select the UV-VIS menu option.

5. Initialize the instrument with 2 μL molecular grade water.

6. When the scanning window appears make sure the 'HiAbs' feature is clicked "on" with a check mark in the appropriate box.

7. Blank the NanoDrop™ with 2 μL 2-HP blank solution. 'Reblank' to validate a flat baseline. If necessary, clean the pedestal and re-blank until a suitable baseline is obtained. Clean the pedestal dry with a Kimwipe.

8. Scan a 2 μL drop 4FB-Oligo sample on the pedestal by clicking the 'Measure' icon. Both black (1 mm) and red trace (0.1 mm) scans should appear.

9. Read the displayed absorbance at A360 (black trace) by toggling the 'λ2 toggle switch' with the mouse until it reaches 360 nm. Record the A360 (black trace-1 mm path length) as displayed in the λ2 window.

10. Obtain the A260 value (red trace—0.1 mm path length) by toggling the 'Max Absorbance toggle switch' downward until the A260 from the red trace is just under full scale in the scan window. Then using the mouse, click the cursor inside the 'Max Absorbance' window and enter a new, slightly higher value until the red trace just reaches full scale in the scan window. When the red trace is adjusted to full scale, read the A260 value displayed in the 'Max Absorbance' window. Record the A260.

Note—numerical entries in the 'Max Absorbance' window can be made in increments of 0.01 A units until the red trace exactly reaches full scale.

11. Enter the resulting A360 and A260 values into the Conjugation Calculator (Section E, green cells). The calculator then displays the 4FB molar substitution ratio or MSR (Section E, yellow cell). The calculator also displays a warning if the 4FB MSR is too low or too high (e.g. less than 0.5 and greater than 1.1). Do not proceed if the measured 4FB ratio is outside the required range.

12. If 4FB-MSR of the oligo is determined to be in the acceptable range (e.g. greater than 0.5 and less than 1.1), transfer the 4FB-oligonucleotide still in the concentrator unit to a new 1.5 mL tube. Label the tube with the MSR and the OD260/μL and store at 4° C. for 1 month or up to 1 year at −20° C. This is the end of Stage 1 and a convenient stopping place.

Note—An "ACCEPTABLE MSR" is displayed if the oligo is at least 50% 4FB-modified (i.e. MSR=0.5). MSR values lower than 50% can occur for various reasons including the absence of the amino-group or insufficient purity of the oligo. Do not proceed if the calculated 4FB MSR is lower than 0.5. A value greater than 1.0 is occasionally observed and is usually the result of incomplete desalting (slight excess of Sulfo-S-4FB carryover). Values up to 1.1 are acceptable but an additional desalting/concentration cycle as previously described (Section G) is recommended when values greater than 1.1 are observed.

4FB Molar Substitution Assay (Conventional Spectrophotometer)

1. Prepare the 2-HP blank solution by adding 2 μL Solution C to 18 μL 2-HP Reagent; label '2-HP Blank'.

2. Prepare a 4FB-oligo sample by adding 2 μL 4FB-modified oligo (0.3-0.6 OD260/μL) to 18 μL 2-HP reagent; label '4FB-Oligo'.

3. Incubate the 2-HP blank and 4FB-Oligo reactions at 37° C. for 30 minutes.

4. Prepare a 1:10 dilution of the 2-HP blank by transferring 10 μL from the completed reaction mixture into 90 μL molecular grade H$_2$O then prepare a 1:100 dilution of the 2-HP blank by transferring 10 μL from the 1:10 2-HP blank dilution into a second tube containing 90 μL molecular grade H$_2$O. Label both tubes appropriately.

5. Prepare a 1:10 dilution of the 4FB-oligo by transferring 10 μL from the completed reaction mixture into 90 μL molecular grade H$_2$O then prepare a 1:100 dilution of the 4FB-oligo by transferring 10 μL from the 1:10 4FB-oligo dilution into a second tube containing 90 μL molecular grade H$_2$O. Label both tubes appropriately.

6. In a quartz micro-cuvette blank the spectrophotometer with 90 μL 1:10 2-HP blank at 360 nm. Remove the blank solution from the cuvette.

7. Measure the A360 of the 1:10 4FB-Oligo sample in the cuvette. Record the A360. Clean the cuvette.

8. Reblank the spectrophotometer using the 1:100 2-HP blank at 260 nm. Remove the blank solution from the cuvette.

9. Measure the A260 of the 1:100 4FB-oligo sample. Record the A260. Clean the cuvette.

10. Enter the resulting A360 and A260 values into the Conjugation Calculator (Section E, green cells). The calculator then displays the 4FB molar substitution ratio or MSR (Section E, yellow cell). The calculator will display a warning if the 4FB MSR is too low or too high (e.g. less than 0.5 and greater than 1.1).

11. If 4FB-MSR of the oligo is determined to be in the acceptable range (e.g. greater than 0.5 and less than 1.1), transfer the 4FB-oligonucleotide still in the concentrator unit to a new 1.5 mL tube. Label the tube with the MSR and the OD260/μL and store at 4° C. for 1 month or up to 1 year at −20° C. This is the end of Stage 1 and a convenient stopping place.

Note—An "ACCEPTABLE MSR" is displayed if the oligo is at least 50% 4FB-modified (i.e. MSR=0.5). MSR values lower than 50% can occur for various reasons including the absence of the amino-group or insufficient purity of the oligo. Do not proceed if the calculated 4FB MSR is lower than 0.5. A value greater than 1.0 is occasionally observed and is usually the result of incomplete desalting (slight excess of Sulfo-S-4FB carryover). Values up to 1.1 are acceptable but an additional desalting/concentration cycle as previously described (Section G) are recommended when values greater than 1.1 are observed.

Stage 2: Modification of Antibody with S-HyNic

Antibodies are packaged in two different physical forms, solids and liquids. Individual samples can vary greatly from vendor to vendor and are often sold in a variety of different sizes and/or concentrations. In all cases, Solulink highly recommends starting with the highest quality/purity antibody available. Depending on the initial form (solid or liquid) follow the instructions that apply to your particular sample.

A. Antibody Preparation; If the IgG is in a solid lyophilized form (100 µg)

1. Add 100 µL Solution B to lyophilized antibody (100 µg solid). Cap the sample vial and vortex for 1 minute.

2. Open the lid and using a P-100 gently pipette the solution up and down while rinsing the wall of the container from top to bottom. Lyophilized antibody can often adhere to the upper walls of a product vial. Visually inspect the vial and lid for any residual lyophilized antibody residue that may have become trapped during the vendor packaging process in order to maximize sample recovery.

Important: although careful resuspension of the antibody is tedious notwithstanding it remains a critical step in the conjugation process. Antibody vendors rarely overfill product vials, so to achieve efficient recovery of expensive antibodies, great care and diligence is recommended.

3. Briefly centrifuge the resuspended antibody at 1,000×g for 10 seconds to collect the entire liquid contents at the bottom of the vial and proceed to confirm antibody concentration.

Note—if the original IgG product is packaged in a product vial that is too large to fit inside a standard microcentrifuge. Such larger vials (e.g. glass vials) can first be placed inside a 50 mL disposable conical tube and briefly spun at 1000×g for 10 seconds using a larger tabletop centrifuge. If a larger tabletop centrifuge is not available, use a rapid and brisk downward flick of the sample vial in an attempt to collect as much of any adhering liquid at the bottom of the vial.

If the IgG is already in liquid form

1. If the initial antibody sample is already in liquid form at 1 mg/ml, transfer 100 µl to another labeled tube (100 µg). If the initial antibody sample is in liquid form at a concentration greater than 1 mg/ml, transfer a volume equivalent to 100 µg to another tube and add the necessary volume (µL) of Solution B to obtain 100 µL at 1 mg/ml. And finally, if the initial antibody sample is less than 1 mg/ml, the sample must first be concentrated to 1 mg/mL and 100 µL using a suitable ultrafiltration spin filter. Spin filters are available from various vendors (e.g. Amicon or Sartorius). An ultra-filtration spin filter is not provided with this kit.

2. Briefly centrifuge the resuspended antibody at 1,000×g for 10 seconds to collect the entire liquid contents at the bottom of the original vial and proceed to confirm antibody concentration.

Note—if the original IgG product is packaged in a product vial that is too large to fit inside a standard microcentrifuge. Such larger vials (e.g. glass vials) can first be placed inside a 50 mL disposable conical tube and briefly spun at 1000×g for 10 seconds using a larger tabletop centrifuge. If a larger tabletop centrifuge is not available, use a rapid and brisk downward flick of the sample vial in an attempt to collect as much of any adhering liquid at the bottom of the vial.

B. Confirm Antibody Concentration on a Spectrophotometer

Confirm the resuspended antibody concentration by measuring the sample's A280 on a spectrophotometer. As before, either a micro-volume UV-VIS scanning spectrophotometer (e.g. NanoDrop™ ND-1000) or conventional spectrophotometer can be used. When using a conventional spectrophotometer a quartz micro-cuvette (50-100 µL, 1-cm path length) is required. Use the appropriate instructions that follow depending on the specific type of spectrophotometer available to you (NanoDrop™ or Conventional).

Antibody Concentration on a NanoDrop™ Spectrophotometer

1. Launch the NanoDrop™ software by clicking the desktop icon.

2. Select the A280 menu option.

3. Initialize the instrument with 2 µL molecular grade water on a clean pedestal.

4. When the scan window appears turn off the 340 nm normalization feature by clicking the appropriate box. Note: some NanoDrop™ instruments do not have a 340 nm normalization feature and ignored for those instruments.

5. Blank the spectrophotometer using 2 µL of the appropriate buffer blank solution (e.g. the solution used to resuspend the antibody). Click the "Reblank" icon to verify a flat baseline (i.e. no offsets).

6. Clean the pedestal and measure the A280 of the antibody sample with a 2 µL aliquot of antibody sample. Record the A280.

7. Enter the name of the antibody, the measured A280 (10 mm path length) and the total volume of antibody solution into the Conjugation Calculator (Section F, green cells). The calculator displays the protein concentration (mg/mL) and the total mass of antibody to be conjugated into the Conjugation Calculator (Section F, yellow cells). A concentration of 1±0.2 mg/mL is required to proceed, otherwise obtain additional IgG or adjust the concentration to 1 mg/mL.

Note—the calculator uses the "average" known mass extinction coefficient (E1%) of IgG to calculate protein concentration (e.g. E1%=14)

Antibody Concentration on a Conventional Spectrophotometer

1. Blank the spectrophotometer at 280 nm using an appropriate blank solution (e.g. the solution used to resuspend the antibody) with a quartz micro-cuvette (50-100 µL, 1-cm path length). Empty the cuvette.

2. Measure the A280 of the antibody sample. Record the A280 and recover the antibody sample from the cuvette back to its sample tube.

3. Enter the name of the antibody, the A280 (1-cm path length) and the volume of antibody solution (e.g. 100 µL) into the Conjugation Calculator (Section F, green cells). The calculator then displays the protein concentration (mg/mL) and total mass of antibody available to be conjugated into the Conjugation Calculator (Section F, yellow cells). A concentration of 1±0.2 mg/mL is required to proceed, otherwise obtain additional IgG or adjust the concentration to 1 mg/mL.

Note—The calculator uses the "average" known mass extinction coefficient (E1%) of IgG to calculate protein concentration (E1%=14).

C. Buffer Exchange Antibody

1. Prepare a spin column (red cap) by twisting off the bottom closure and loosening the red cap (do not remove). Place the spin column into a collection tube (provided).

2. Mark the top of the red cap using an indelible pen to identify the antibody sample. Also place a vertical mark on the side of the spin column as shown below.

3. Place the entire assembly into the centrifuge and orient the vertical mark on the spin column aiming outward and away from the center of the rotor. Use an appropriate balance tube opposite the spin column.

4. Centrifuge at 1,500×g for 1 minute. Discard the flow through from the collection tube. The column matrix will appear white in color. Place the column back into a new empty collection tube (provided).

5. Open the red cap; load the antibody sample (~100 µL at 1 mg/mL) to the top of the dry resin bed; loosely cap and place the column back into the collection tube.

6. Orient the spin column mark outward as before and centrifuge at 1,500×g for 2 minutes.

7. Transfer the eluate from the bottom of the collection tube to a new labeled 1.5 mL tube; measure the volume (µL) recovered from the collection tube with a P-200 pipette. Label the tube with the appropriate volume (µL) recovered.

D. Dissolve S-HyNic Reagent

1. Add 35 µL DMF to a vial of S-HyNic reagent. Pipette the solution up and down for 60 seconds to dissolve the pellet.

E. Modify IgG with S-HyNic Reagent and Buffer Exchange

1. Add 2.0 µL of dissolved S-HyNic modification reagent to the antibody sample. Gently pipette the solution to mix.

2. Incubate the antibody/HyNic modification reaction at room temperature for 2 hours.

3. Exactly five minutes prior to the end of the HyNic modification reaction, prepare a spin column (yellow cap) by twisting off the bottom closure and loosening the cap (do not remove). Place the spin column into a collection tube and mark the top of the yellow cap with an indelible pen to identify the antibody sample. Also place a vertical mark on the side of the spin column as shown on below.

4. Place the assembly into the centrifuge and balance appropriately. Orient the mark on the side of the spin column aiming outward and away from the center of the rotor. Use an appropriate balance tube opposite the spin column.

5. Centrifuge at 1,500×g for 1 minute. Discard the flow through from the bottom of the collection tube. The column matrix will appear white in color. Place the column back into a new empty collection tube (provided).

6. After the HyNic modification reaction is complete, apply the HyNic/IgG reaction mixture (~100 µL) to the top of the dry resin bed. Loosely recap and orient the spin column in the centrifuge. Centrifuge at 1,500×g for 2 minutes.

7. Transfer the recovered volume (µL) of HyNic-modified IgG using a P-200 pipette from the bottom of the collection tube to a new 1.5 mL tube. Measure and record the volume recovered and immediately proceed to conjugate formation.

Stage 3: Formation of Conjugate and Purification

A. Conjugate Formation

1. Enter the name of the antibody, the name of the 4FB-oligonucleotide, and the volume of HyNic-IgG to be conjugated into the Conjugation Calculator (Section G, green cells).

2. Add the indicated volume (µL) of 4FB-modified oligonucleotide displayed in the Conjugation Calculator (Section G, yellow cell) to the HyNic-modified antibody. Pipette the solution up and down to mix.

3. Incubate the antibody-oligo conjugation reaction for 2 hr at room temperature.

4. At the end of the conjugation reaction, quench the reaction by adding 10 µL Conjugate Quench Reagent and incubate for 10 minutes at room temperature.

B. Conjugate Purification

1. Centrifuge the vial containing affinity magnetic beads (black slurry) at 1000×g for 5 seconds to collect the bead contents at the bottom of the tube.

2. Add 500 µL Solution C to the bead slurry; using a P-1000 pipette, pipette the solution up and down several times to mix the slurry. Quickly before the beads resettle place the tube on the magnet for 10 seconds; carefully remove and discard the supernatant using a P-200 pipette without disturbing the pellet.

3. Repeat step 2 three (3) additional times to fully wash the beads; removing the supernatant after each wash.

4. Immediately add the quenched conjugation reaction (~115 µL) directly to the washed bead pellet.

5. Gently pipette the slurry/conjugate mix up and down 3-4 times with a P-1000 (barrier tips). Set a timer and allow the settled slurry to incubate for 10 minutes away from a magnet. Never vortex beads after conjugate addition. Set P-1000 to 90 µL when mixing slurry.

6. Repeat step five three (3) additional times for a total conjugate binding time of 40 minutes. Some minor but unavoidable bead loss can occur due to non-specific binding of beads inside the pipette tip.

7. Gently pipette the settled slurry up and down one last time and immediately place the slurry on the magnet for 10 seconds before the beads have a chance to resettle.

8. The conjugate is now bound to the affinity matrix. With a P-200 pipette, carefully remove and discard the supernatant without disturbing the magnetized bead pellet.

9. Immediately add 500 µl Solution D to the bead pellet, remove the tube from the magnet and pipette the slurry up and down with a P-1000 several times to wash. Never vortex the beads. Before the beads resettle; place them back on the magnet for 10 seconds. Remove and discard the supernatant without disturbing the pellet.

10. Repeat step 9 three (3) additional times; discarding the wash supernatant between washes.

11. Remove the tube from the magnet and add 100 µL Solution E directly to the bead pellet.

12. Using a P-1000, pipette the slurry up and down until the bead pellet adhered to the wall is rinsed to the bottom of the vial. Never vortex the beads. Set P-1000 to 90 µL when mixing slurry.

13. Incubate the settled slurry for 5 minutes away from the magnet.

14. Mix the slurry up and down and incubate for another 5 minutes away from the magnet.

15. Repeat step 14 one (1) additional time. Total conjugate elution time for these three elution/incubation periods is 15 minutes.

16. Pipette the settled slurry up and down with the P-1000 one last time and immediately place the slurry on the magnet for 10 seconds before the beads have a chance to resettle 17. Without disturbing the pellet, carefully transfer the clarified supernatant (~100 µl) containing the eluted conjugate to a new labeled 1.5 mL tube.

18. Repeat step 11-17 one (1) additional time; pooling the two 100 µL conjugate fractions together in the same tube (200 µL final volume). Buffer exchange the eluted conjugate into storage buffer.

C. Buffer Exchange into Storage Buffer

Prepare two spin columns (blue cap) by twisting off the bottom closure and loosening the cap (do not remove the cap). Place each spin column into a collection tube (provided) and mark the top of the blue caps with an indelible pen to identify the conjugate. Also place a vertical mark on the side of the spin column as shown on below.

1. Place the two spin columns in the centrifuge and orient the vertical mark on the spin column aiming outward and away from the center of the rotor.

2. Centrifuge at 1,500×g for 1 minute. Discard the flow through from each collection tube. Each column matrix will appear white in color. Place the columns back into new empty collection tubes (provided).

3. Open each blue cap; load 100 μL conjugate to the top of each dry resin bed; loosely cap and place them back into their empty collection tube.

4. Orient the spin column mark outward as before and centrifuge at 1,500×g for 2 minutes.

5. Eluted conjugate is now in storage buffer at the bottom of the two collection tubes. Pool the two 100 μL fractions containing antibody-oligo conjugate into a single 1.5 mL tube. Label and store the tube at 4° C. for up to 1 year.

6. Measure the protein concentration of the conjugate using a Bradford protein assay as described in the Appendix.

A. Bradford Protein Assay

A Bradford or BCA Protein Assay is used to determine the final antibody-oligonucleotide conjugate concentration. A reference protocol is provided for each procedure.

Bradford 96-Well Procedure
Required Materials
Bradford Reagent (Bio-Rad, Hercules, Calif., Cat. #500-0006)
96-well plate (polystyrene flat bottom)
PBS (Phosphate Buffered Saline)
P-200 and P-1000 pipettes and sterile tips
Bovine IgG Antibody Standard: 2 mg/ml (Pierce/ThermoFisher, Cat. # #23212)
Molecular grade water Assay Protocol 1. Prepare 2 mL of Bradford working solution by adding 400 μL Bradford dye reagent to 1600 μL molecular grade water (1:4 ratios).

Prepare IgG standards and a blank in 1.5 mL tubes as follows:

Add 100 μL 2 mg/mL bovine IgG standard to 300 μL PBS (0.5 mg/mL standard)

Add 200 μL 0.5 mg/ml standard to 200 μL PBS (0.25 mg/mL standard)

Add 200 μL 0.25 mg/mL standard to 200 μL PBS (0.125 mg/mL standard)

Add 200 μL 0.125 mg/mL standard to 200 μL PBS (0.0.0625 mg/mL standard)

100 μL PBS (buffer blank)

2. In a flat-bottom 96-well plate, prepare standards by pipetting 10 μL of each standard (and a blank) into 100 μL Bradford working solution; mix. Replace pipette tips between additions.

3. In an adjacent well containing 100 μL Bradford working solution add 10 μL of the conjugate.

4. Incubate at room temperature (18-25° C.) for 15 min (do not exceed 60 min).

5. Measure absorbance at 595 nm using pre-programmed Bradford assay software.

Figure 24:
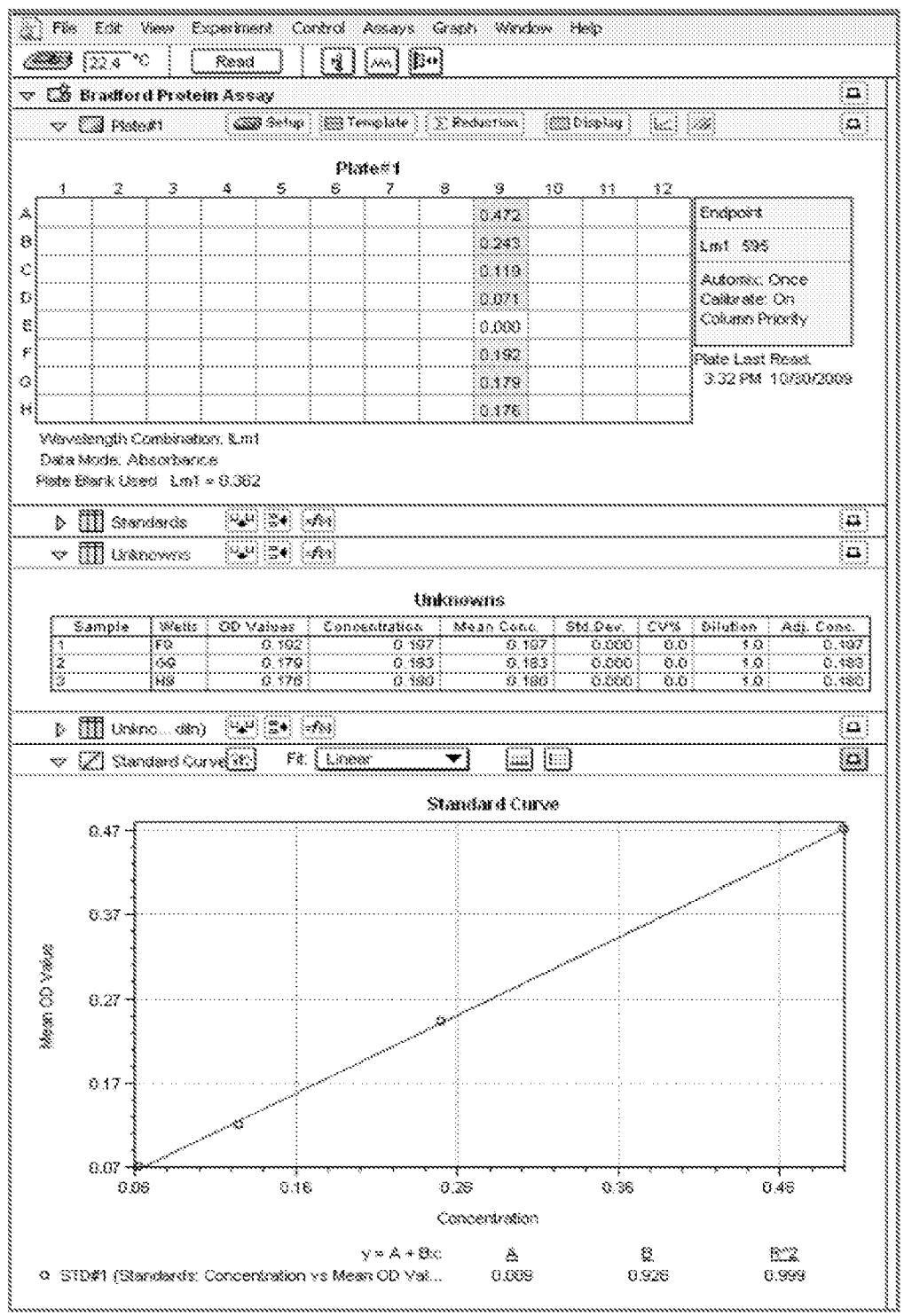
FIG. 24: Bradford output from a commercial plate reader
Figure 25:
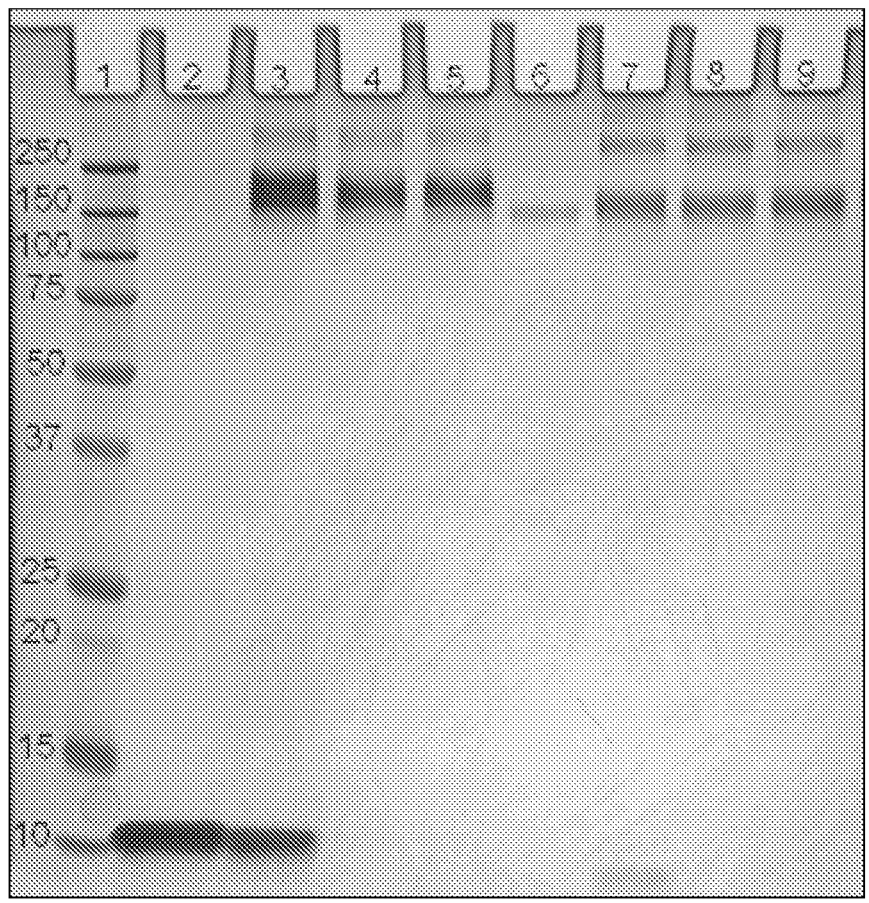
FIG. 25: Illustration of a gel comprising: Mouse mAb/oligonucleotide conjugates (44-mer and 22-mer): A. 1) Protein Molecular Weight Marker; 2) 4FB-Oligonucleotide 44-mer; 3) Crude mouse anti-FITC mAb/44-mer reaction 800 ng; 5) Duplicate of lane 4; 6) Mouse anti-FITC mAb 200 ng; 7) Crude mouse anti-FITC mAb/22-mer conjugation reaction 800 ng; 8) Affinity purified mouse anti-FITC mAb/22-mer reaction 800 ng; 9) Duplicate of lane 8. Wherein the gel was stained with B. Silver stain 10% SDS PAGE SDS/MOPS.
Figure 26:
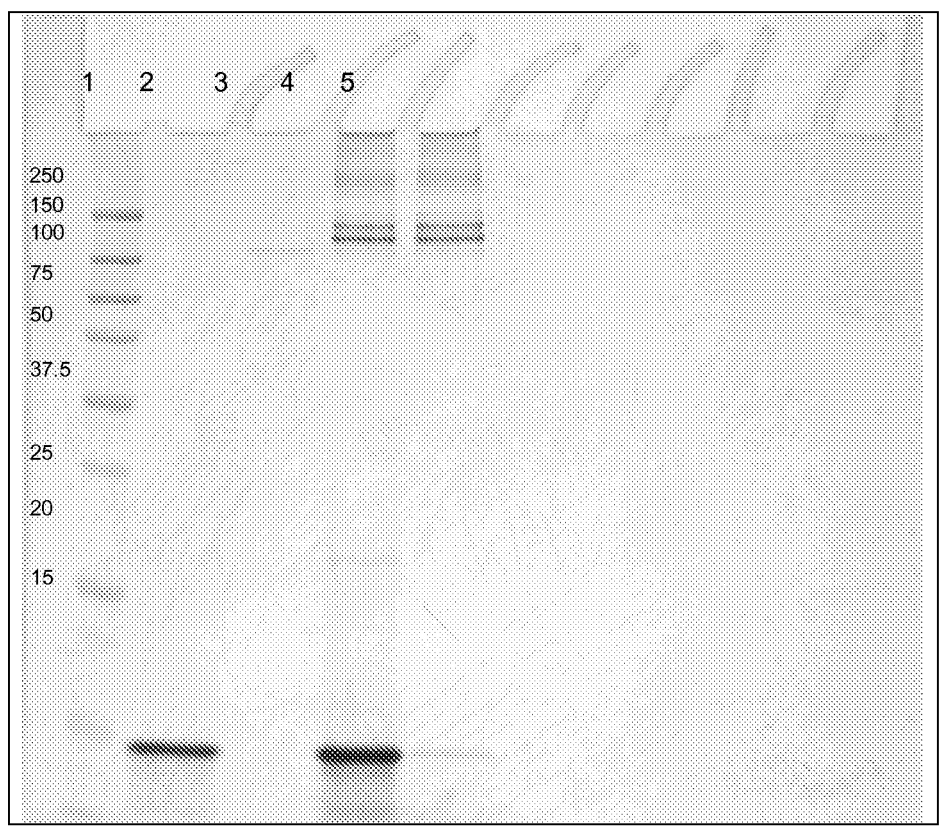
FIG. 26: Hamster mAb/oligonucleotide conjugate (60-mer): A. 1) Protein molecular weight marker; 2) 60-mer 4FB-oligonucleotide standard; 3) Hamster mAb anti-CD3 145-C211 standard (250 ng); 4) All-in-One™ crude conjugation reaction (60-mer/anti-DC3 mAb) 900 ng protein; 5) Affinity purified anti CD3-60-mer antibody-oligonucleotide conjugate 900 ng protein. Wherein the gel was stained with B. Silver Stain Gel MOPS/SDS Buffer 12% NU-PAGE SDS-Gel.

6. Data from a typical Bradford assay is provided as an illustration only in FIG. 24.

A. The Troubleshooting Guide as shown below in Table 3.

TABLE 3

| Problem | Possible Cause | Recommended Action |
|---|---|---|
| Poor conjugate yield Poor or undetectable conjugate yield | Amino-oligonucleotide may not be sufficiently 4FB-modified Quality and/or purity of starting antibody is poor | Verify 4FB MSR to insure proper conjugation. Concentrate 4FB-oligo into the required range (0.3-0.6 OD260/μL). If antibody quality or source are undetermined, perform suitable test such as SDS-gel page analysis and/or a Bradford protein assay to confirm the purity and quantity of the starting material |
| Poor HyNic modification | Presence of protein carriers such as BSA or gelatin may be contaminating antibody sample. | Remove and purify the antibody sample of all protein carriers such as BSA or gelatin using affinity chromatography or other method before proceeding. |
| Poor HyNic modification Poor HyNic modification | Concentration of S-HyNic modification reagent Presence of non-protein amine contaminants Improper storage of S-HyNic reagent can lead to hydrolysis of the NHS ester initial antibody concentration is low | Make sure to thoroughly dissolve S-HyNic reagent before adding it to the antibody. Use a calibrated pipette to insure accuracy in small volume additions. Remove all non-protein amine contaminants such as glycine or Tris before modifying the antibody with S-HyNic reagent. Keep and store the S-HyNic reagent sealed in the pouch provided below 4° C. Confirm initial antibody concentration prior to S-HyNic modification on the spectrophotometer. If in doubt perform a Bradford Dissolve the antibody sample carefully in the original product vial. |
| Low conjugate and/or | Low buffer exchange spin | Use a properly calibrated variable- |

TABLE 3-continued

| Problem | Possible Cause | Recommended Action |
|---|---|---|
| antibody recovery | column recovery volume Low yield during affinity purification of conjugate | speed centrifuge and follow recommended spin speed/time. Altered spin speeds will adversely compromise recovery. Make sure to follow all the incubation times for binding and elution of conjugate. |

EXAMPLES

The following examples and protocols are given as particular embodiments of the disclosure and to demonstrate the advantages thereof. It is understood that the examples and protocols are given by way of illustration and are not intended to limit the specification or the claims that follow. Additional information is also found in the attached SoluLink manual, entitled Antibody-Oligonucleotide All-in-One Conjugation Kit User Manual, Catalog No. A-9201-001.

The conjugation examples below include a (1) HyNic antibody modification step, (2) conversion of an amino-oligonucleotide to a 4FB-oligonucleotide and (3) conjugation step. Following are common procedures used in the Examples that follow.

Antibody-HyNic Modification: The antibody is exchanged into Modification Buffer (100 mM phosphate, 150 mM NaCl, pH 7.4) and a solution of S-HyNic in anhydrous DMF (X equivalents as described below) are mixed and incubated at room temperature for 1.5 h. The HyNic-antibody is purified to remove excess modification reagent and simultaneously buffer exchanged into Conjugation Buffer (100 mM phosphate, 150 mM NaCl, pH 6.0) using a Zeba desalting column (ThermoPierce, Rockford, Ill.).

4FB-oligonucleotide preparation: 3'- or 5'-amino-modified oligonucleotide is exchanged into Modification Buffer and the concentration is adjusted between 0.2 and 0.5 OD/uL. To the required volume of amino-oligonucleotide is added a ½ volume of DMF followed by addition of S-4FB (20 equivalents in DMF). The reaction is incubated at room temperature for 1.5 hours, diluted to 400 μL with Conjugation Buffer (100 mM phosphate, 150 mM NaCl, pH 6.0) and desalted using a 5K MWCO Vivaspin diafiltration apparatus. The 4FB-modified oligonucleotide is washed with Conjugation Buffer (3×400 uL), the OD/uL of the purified oligonucleotide is determined and used directly in the following conjugation reaction.

HyNic-antibody/4FB-oligonucleotide conjugation: To the HyNic-antibody (1 mol equiv) in conjugation buffer is added 4FB-oligonucleotide (3-5 equiv as described in the experiments). To the reaction mixture is added 1/10th volume TurboLink Buffer (100 mM aniline, 100 mM phosphate and 150 mM NaCl, pH 6.0. The reactions are incubated for 2 hours and purified as described below.

The gel data in the Figures were run on 4-12% Novex Bis-tris gels (Invitrogen, Carlsbad, Calif.) using MOPS Running Buffer (Invitrogen). Samples were loaded using NuPage LDS Sample Buffer (Invitrogen) without DTT or heating prior to loading.

Gels were developed as indicated with Coomassie blue for visual protein detection, Lumetein protein stain (Biotium, Hayward, Calif.) or DNA DNA Silver Stain (GE Healthcare, Piscataway, N.J.).

Example 1

Figure 2:
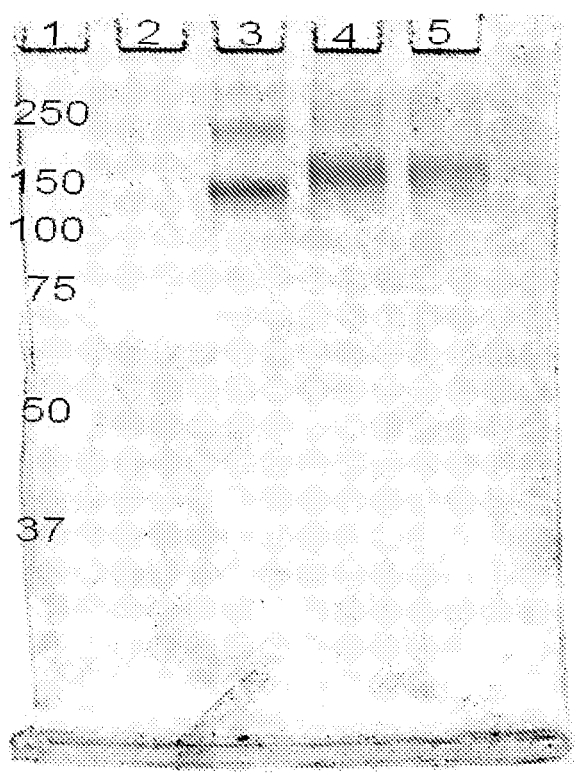
FIG. 2 is a gel electrophoresis loading 400 ng of antibody with Lumitein stain, containing the following lanes: Marker (lane 1); SFB-H1A (lane 2); HyNic-Bovine IgG (lane 3); Bovine IgG/H1A crude (lane 4) and Bovine IgG/H1A purified (lane 5), in accordance with certain embodiments.
Figure 3:
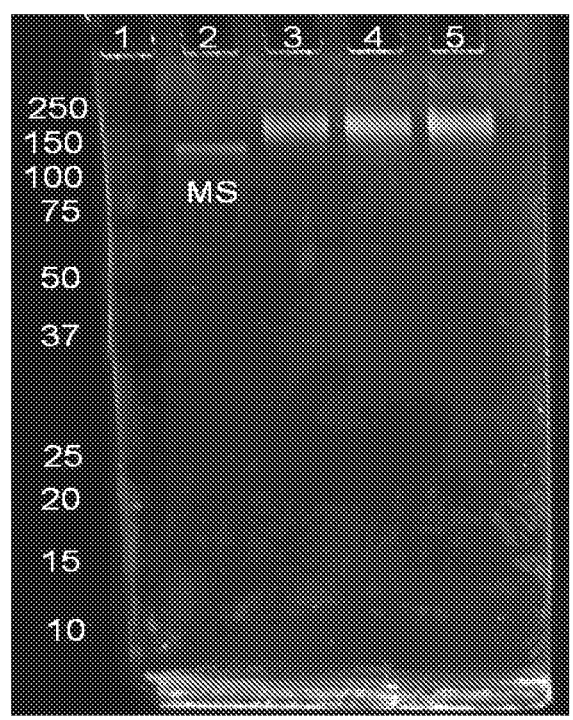
FIG. 3 is a gel electrophoresis loading 500 ng of antibody with Commassie stain, containing the following lanes: Marker (lane 1); SFB-H1A (lane 2); HyNic-Bovine IgG (lane 3); Bovine IgG/H1A crude (lane 4) and Bovine IgG/H1A purified (lane 5), in accordance with certain embodiments.
Figure 4:
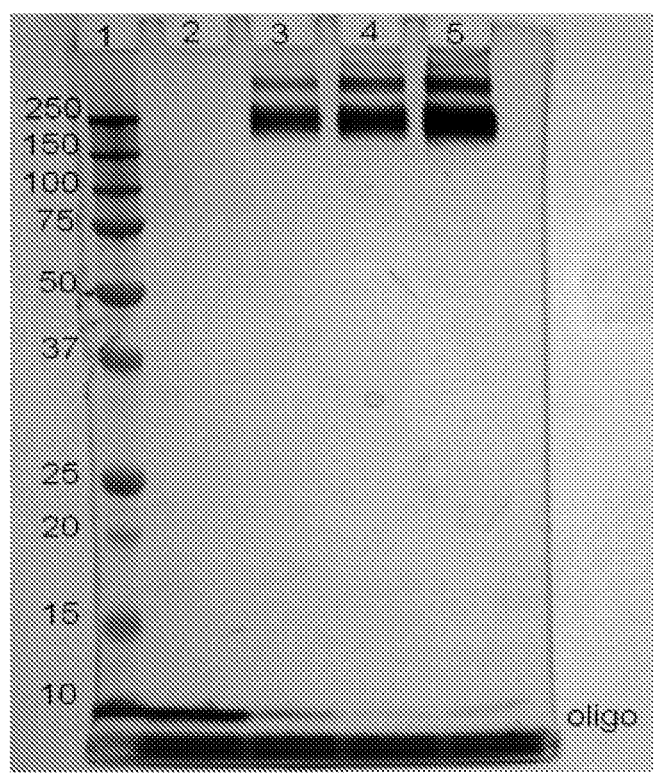
FIG. 4 is a gel electrophoresis with Lumitein stain, containing the following lanes: Marker (lane 1); HyNic-MS anti-FITC 150 ng (lane 2); MS anti-FITC/H1A crude 300 ng (lane 3); MS anti-FITC/H1A purified 300 ng (lane 4) and MS anti-FITC/H1A purified 450 ng (lane 5), in accordance with certain embodiments.

In this Example a polyclonal antibody (bovine IgG (bIgG)) and a mouse monoclonal antibody (anti-FITC monoclonal antibody; Jackson ImmunoResearch (Chadds Ford, Pa.)) were modified at 4 mg/mL with S-HyNic (20 equivalents). Following desalting into Conjugation Buffer the HyNic-antibodies were treated with a 35mer 5'-4FB oligonucleotide (5 equivalents). The conjugates were purified using USY-20 size exclusion Ultrafiltration Units (Advantec MFS, Inc., Dublin, Calif.). The DNA Silver stained PAGE results for conjugation to bIgG are presented in FIG. 1. The loading, stain and samples in each lane are:
  Loading: 400 ng antibody
  Visualization/stain: Sybr Gold stain
  Lane 1. Marker
  Lane 2. 4FB-35mer oligonucleotide
  Lane 3. HyNic-Bovine IgG
  Lane 4. Bovine IgG/4FB-35mer oligonucleotide crude
  Lane 5. Bovine IgG/4FB-35mer oligonucleotide purified The Lumetein stained PAGE results for conjugation to β-IgG are presented in FIG. 2. As shown in the gel in FIG. 2, there is significant conversion of antibody to conjugate. Lane 4 presents the shift of the product band to higher molecular weight and minor amounts of starting antibody as compared to Lane 3. In that the sensitivity of Lumetein fluorescent protein stain is 1 ng this result would indicate greater than 90% conversion of antibody to conjugate as 400 ng of antibody were loaded in each lane. The loading, stain and samples in each lane are:
  Loading: 400 ng antibody
  Visualization/stain: Lumetein stain (Biotium; Hayward, Calif.)
  Lane 1. Marker
  Lane 2. 4FB-35mer oligonucleotide
  Lane 3. HyNic-Bovine IgG
  Lane 4. Bovine IgG/4FB-35mer oligonucleotide crude
  Lane 5. Bovine IgG/4FB-35mer oligonucleotide purified The Lumetein stained PAGE results for conjugation to anti-FITC monoclonal antibody are presented in FIG. 3. No unconjugated antibody is seen in lanes 3, 4 and 5 therefore based on the efficiency of conversion of antibody to conjugate is greater than 95% based on the sensitivity of the Lumetein stain. The loading, stain and samples in each lane are:
  Loading: 150 ng antibody
  Visualization/stain: Lumetein stain
  Lane 1. Marker
  Lane 2. HyNic-MS anti-FITC 150 ng
  Lane 3. MS anti-FITC/4FB-35mer oligonucleotidecrude 300 ng
  Lane 4. MS anti-FITC/4FB-35mer oligonucleotide purified 300 ng
  Lane 5. MS anti-FITC/4FB-35mer oligonucleotide purified 450 ng The DNA Silver stained PAGE results for conjugation to anti-FITC monoclonal antibody are presented in FIG. 4. Unconjugated oligo can be seen in both lanes 4 and 5 demonstrating the inefficiency in removing excess oligonucleotide using the USY 20 diafiltration filter. The sensitivity of DNA Silver Stain is ~50 pg oligo.

The loading, stain and samples in each lane are:
Loading: 150 ng antibody
Visualization/stain: Lumetein stain
Lane 1. Marker
Lane 2. HyNic-MS anti-FITC 150 ng
Lane 3. MS anti-FITC/4FB-35mer oligonucleotide crude 300 ng
Lane 4. MS anti-FITC/4FB-35mer oligonucleotide purified 300 ng
Lane 5. MS anti-FITC/4FB-35mer oligonucleotide purified 450 ng Example 2

This experiment compares purification of antibody-oligonucleotide conjugates by diafiltration and adsorbing the conjugate on a Zinc-chelate modified magnetic bead, washing the beads with buffer to remove excess 4FB-oligonucleotide and eluting the conjugate from the bead with imidazole-based eluting buffer.

Crude conjugate mixture prepared in Example 1 was purified by either a 100 kD MWCO Vivaspin diafiltration spin column or Zinc-magnetic-bead to remove free oligo:
(A) Diafiltration purification: Conjugate was diluted into PBS (400 uL) placed in the diafiltration apparatus and concentrated. The retentate was diluted with PBS and concentrated 3 more times.
(B) Zinc-chelate-magnetic-bead purification: Added crude conjugated antibody/oligo mixture to Zn-SepFast Mag (Biotoolmics, UK) and bind for 30-40 min. The beads were washed (0.4 mL) with 25 mM sodium phosphate, 300 mM sodium chloride, 0.05% Tween-20, pH 7.5 4 times. The conjugate was eluted from the beads with 25 mM EDTA, 300 mM NaCl, 250 mM Imidazole, 75 ug/mL HIS-6 peptide (SEQ ID NO: 1), pH 6.0, 4 times. The purified conjugate was exchanged into 10 mM sodium phosphate, 149 mM sodium chloride, 1 mM EDTA, 0.05% sodium azide, pH 7.2.

Figure 5:
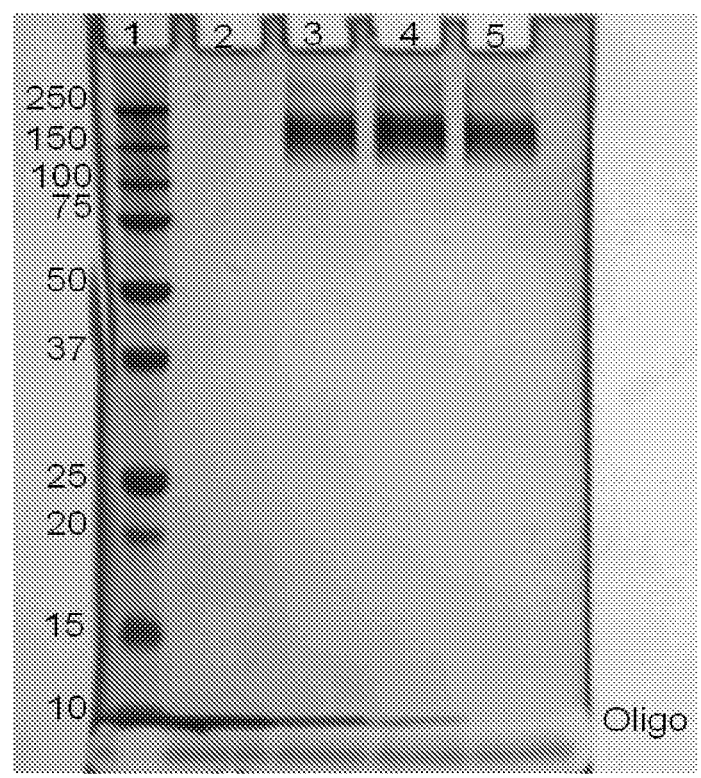
FIG. 5 is a gel electrophoresis loading 300 ng of antibody with DNA Silver stain containing the following lanes: Marker (lane 1); 4FB-H1A (lane 2); Bovine IgG/H1A crude (lane 3); Bovine IgG/H1A purified with Diafiltration spin column 100K (lane 4) and Bovine IgG/H1A purified Zinc-His-tag-magnetic-bead (lane 5), in accordance with certain embodiments.

As shown in FIG. 5, loading 300 ng of antibody and developing with DNA Silver stain demonstrated near quantitative removal of excess oligonucleotide by adsorbing Ab-oligonucleotide conjugate on Zinc magnetic beads followed by release as no excess oligo is present in Lane 5 while oligo can be seen in Lane 4. The loading, stain and samples in each lane are:
Loading 300 ng of antibody
Stain: DNA Silver stain
Lane 1. Marker
Lane 2. 4FB-34FB-35mer oligonucleotide
Lane 3. Bovine IgG/34FB-35mer oligonucleotidecrude
Lane 4. Bovine IgG/4FB-35mer oligonucleotide purified with
Diafiltration spin column 100K
Lane 5. Bovine IgG/4FB-35mer oligonucleotide purified Zinc-magnetic-bead
Based on the sensitivity of DNA Silver Stain greater than 98% of the excess is removed using this method.

Example 3

Figure 6:
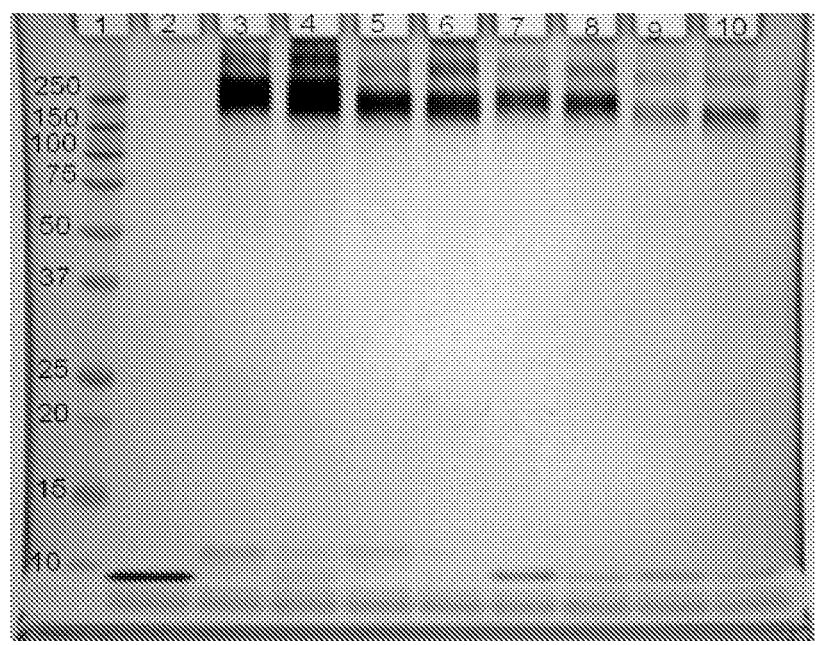
FIG. 6 is a gel electrophoresis loading Loading 300 ng of antibody with Silver stain containing the following lanes: Marker (lane 1); 4FB-46mer 4FB-oligonucleotide (lane 2); 1:5 MS anti-FITC/46mer 4FB-oligonucleotide crude (lane 3); 1:5 MS anti-FITC/46mer 4FB-oligonucleotide purified (lane 4); 1:3 MS anti-FITC/46mer 4FB-oligonucleotide crude (lane 5); 1:3 MS anti-FITC/46mer 4FB-oligonucleotide purified (lane 6); 1:5 MS anti-FITC/36mer 4FB-oligonucleotide crude (lane 7); 1:5 MS anti-FITC/36mer 4FB-oligonucleotide purified (lane 8); 1:3 MS anti-FITC/36mer 4FB-oligonucleotide crude (lane 9) and 1:3 MS anti-FITC/36mer 4FB-oligonucleotide purified (lane 10), in accordance with certain embodiments.

This experiment was designed to determine the optimal number of equivalents of 4FB-oligonucleotide required to be reacted with 1 mol equivalent HyNic-antibody to yield greater than 90% conjugate. To that end a 46mer and a 35mer 4FB oligonucleotide were added to HyNic-anti-FITC antibody at both 3 and 5 mol equiv/mol antibody. The conjugates were purified by adsorption/desorption on Zn-magnetic beads as described in Example 2. The loading, stain and samples in each lane are:
Loading: 300 ng of antibody
Stain: DNA Silver stain
Lane 1. Marker
Lane 2. 4FB-46mer 4FB-oligonucleotide
Lane 3. 1:5 MS anti-FITC/4FB-46mer oligonucleotide crude
Lane 4. 1:5 MS anti-FITC/4FB-46mer oligonucleotide purified
Lane 5. 1:3 MS anti-FITC/4FB-46mer oligonucleotide crude
Lane 6. 1:3 MS anti-FITC/4FB-46mer oligonucleotide purified
Lane 7. 1:5 MS anti-FITC/4FB-35mer oligonucleotide crude
Lane 8. 1:5 MS anti-FITC/4FB-35mer oligonucleotide purified
Lane 9. 1:3 MS anti-FITC/4FB-35mer oligonucleotide crude
Lane 10. 1:3 MS anti-FITC/4FB-35mer oligonucleotide purified The DNA Silver stained PAGE results are presented in FIG. 6, include crude reaction and purified product samples demonstrating that 5 equivalents yielded a conjugate with more oligonucleotides/antibody as deduced by the darker bands in the samples where 5 equivalents of oligonucleotide were added.

Example 4

Figure 7:
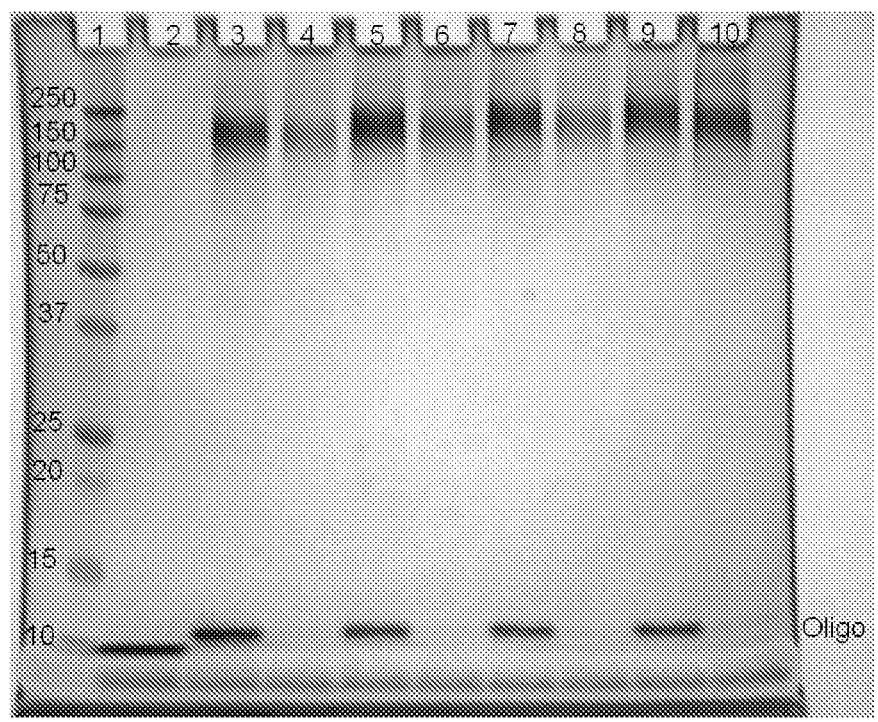
FIG. 7 is a gel electrophoresis loading 300 ng of antibody with Silver stain, containing the following lanes: Marker (lane 1); SFB-H1A (lane 2); 20× Bovine IgG/DG2A crude (lane 3); 20× Bovine IgG/DG2A purified (lane 4); 30× Bovine IgG/DG2A crude (lane 5); 30× Bovine IgG/DG2A purified (lane 6); 40× Bovine IgG/DG2A crude (lane 7); 40× Bovine IgG/DG2A purified (lane 8); 50× Bovine IgG/DG2A crude (lane 9) and 50× Bovine IgG/DG2A purified (lane 10), in accordance with certain embodiments.

This experiment was designed to determine the optimal number of equivalents of S-HyNic to be added to the antibody at 1 mg/mL to yield greater than 90% conversion to conjugate. In one experiment bIgG was reacted with 20×, 30×, 40× and 50× equivalents of S-HyNic and reacted with 5 equivalents of a 46mer 4FB-oligonucleotide. The DNA Silver stained PAGE results are presented in FIG. 7, showing excellent conversion to conjugate in all reactions as evidenced by the dark bands in each lane and as the number of equivalents of S-HyNic are increased the number of oligonucleotides/antibody increases as the conjugate bands penetrate the gel less as the number of equivalents of S-HyNic increases resulting in the conjugation of more oligonucleotides/antibody. The loading, stain and samples in each lane are:
Loading 300 ng of antibody
Stain: DNA Silver stain
Lane 1. Marker
Lane 2. 4FB-35mer oligonucleotide
Lane 3. 20× Bovine IgG/4FB-46mer oligonucleotide crude
Lane 4. 20× Bovine IgG/4FB-46mer oligonucleotide purified
Lane 5. 30× Bovine IgG/4FB-46mer oligonucleotide crude
Lane 6. 30× Bovine IgG/4FB-46mer oligonucleotide purified
Lane 7. 40× Bovine IgG/4FB-46mer oligonucleotide crude
Lane 8. 40× Bovine IgG/4FB-46mer oligonucleotide purified
Lane 9. 50× Bovine IgG/4FB-46mer oligonucleotide crude
Lane 10. 50× Bovine IgG/4FB-46mer oligonucleotide purified Example 5

Figure 8:
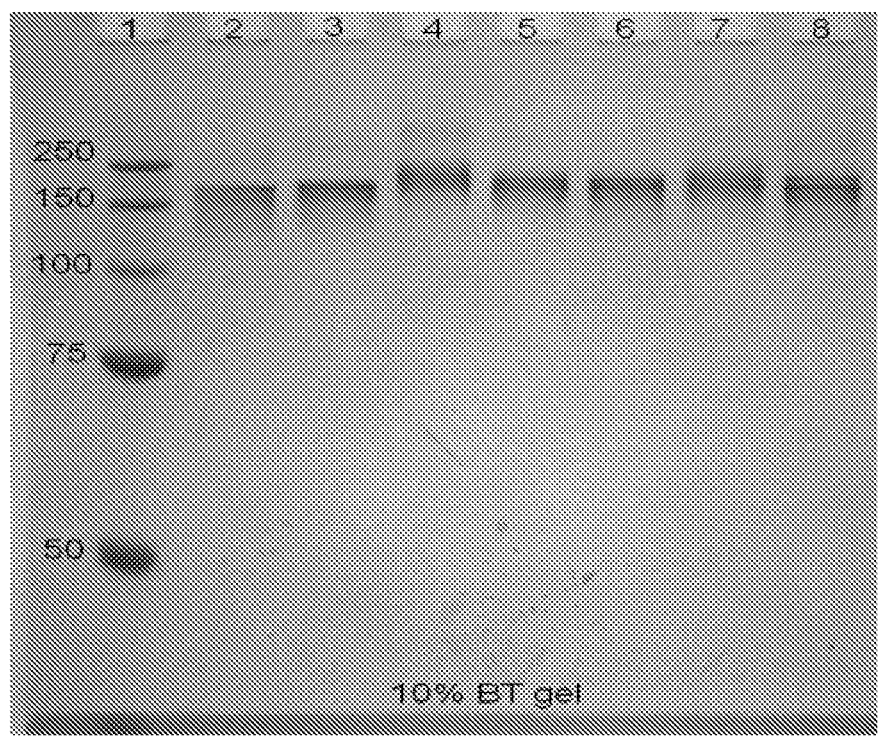
FIG. 8 is a gel electrophoresis 1.0 ug of antibody with Commassie stain, containing the following lanes: Marker (lane 1); HyNic-MS anti-FITC (lane 2); Purified MS anti-FITC/V3B 19 bp (lane 3); Purified MS anti-FITC/H1A 35 bp (Ab 4 mg/ml) (lane 4); Purified MS anti-FITC/Amino-40 40 bp (lane 5); Purified MS anti-FITC/Amino-40 40 bp (lane 6); Purified MS anti-FITC/DG2A 46 bp (lane 7) and Purified MS anti-FITC/Amino-60 60 bp (lane 8), in accordance with certain embodiments.

To determine the effect of length of oligonucleotide on conjugation efficiency 5 mol equivalents of 19mer, 39mer, 40mer, 46mer and 60mer 4FB-modified oligonucleotides were reacted with a anti-Fitc monoclonal antibody that had been modified with 30 equivalents S-HyNic at 1 mg/mL antibody concentration. The DNA Silver stained PAGE results of the purified conjugates are presented in FIG. 8, showing equivalent band density in each lane indicating that 4FB-oligonucletodes for length 19mer to 60mer conjugate with equal efficiency. The loading, stain and samples in each lane are:

Loading 1.0 ug of antibody
Stain: Commassie blue
Lane 1. Marker
Lane 2. HyNic-MS anti-FITC
Lane 3. Purified MS anti-FITC/4FB 19mer 4FB oligonucleotide
Lane 4. Purified MS anti-FITC/4FB-35mer oligonucleotide
Lane 5. Purified MS anti-FITC/4FB-40mer oligonucleotide
Lane 6. Purified MS anti-FITC/4FB-40mer oligonucleotide
Lane 7. Purified MS anti-FITC/4FB-46mer oligonucleotide
Lane 8. Purified MS anti-FITC/4FB-60mer oligonucleotide The yields of the reactions based on BCA Protein Assay (ThermoPierce, Rockford, Ill.) were 55%, 52%, 50%, 50%, 47% and 50% for the 19mer, 39mer, 40mer, 46mer and 60mer 4FB-modified oligonucleotides conjugations respectively.

Example 6

This example presents the preparation and purification of an oligonucleotide/antibody conjugate using the optimized conditions as determined in the Examples above. In this experiment 40mer and 60 mer 5'-amino-oligonucleotides as shown in TABLE 1 were 4FB-modified and conjugated to an antibody that was reacted with 30 equivalents of S-HyNic at 1 mg/mL then purified using the Zn-magnetic bead adsorption/desorption method.

TABLE 4

| # | #Base Pairs | MW | Ext Coeff | Oligonucleotide Sequence |
|---|---|---|---|---|
| Oligo-1 | 40 | 12451.2 | 37400 | 5'-G ACT GAC GAA CCG CTT TGC CTG ACT GAT CGC TAA ATC GTG-NH$_2$ (SEQ ID NO: 2) |
| Oligo-2 | 60 | 18557.1 | 55020 | 5'-TTG CAT CGC CCT TGG ACT ACG ACT GAC GAA CCG CTT TGC CTG ACT GAT CGC TAA ATC GTG-NH$_2$ (SEQ ID NO: 3) |

First, a stock solution of bovine IgG (bIgG) 5 mg/mL in modification buffer (100 mM phosphate, 150 mM NaCl, pH 7.4; Sigma (St. Louis, Mo.)) was prepared. bIgG stock solution (20 uL; 100 ug bIgG) was diluted with modification buffer (80 uL) to prepare a 1 mg/mL solution and was exchanged into modification buffer (using a 0.5 mL Zeba 7K Desalting columns (ThermoPierce, Rockville, Ill.)) pre-equilibrated with modification buffer. A stock solution of S-HyNic (1.0 mg dissolved in anhydrous DMF (200 µL); SoluLink Biosciences (San Diego, Calif.)) was prepared. To the bIgG in modification buffer was added S-HyNic/DMF solution (1.12 µL; 30 mol equivalents). The mixture was mixed thoroughly by pipette and incubated at room temperature for 2.0 h. Using a 0.5 mL Zeba column the reaction mixture was desalted and buffer exchanged into conjugation buffer (100 mM phosphate, 150 mM NaCl, pH 6.0). This HyNic-antibody was used directly in the conjugation reaction.

A 3'-Amino-modified 40mer Oligo-1 (11.1 ODs; Eurogentec (San Diego, Calif.)) was dissolved in 50 mM NaOH (30 µL) and was buffer exchanged into modification buffer using a 0.5 mL Zeba desalting column pre-equilibrated in modification buffer. The OD/µL of the final oligo solution was determined to be 0.33 OD/µL. A stock solution of S-4FB (1.0 mg; SoluLink Biosciences) in anhydrous DMF (25 µL) was prepared. To the desalted oligo was added DMF (15 µL) followed by S-4FB/DMF solution (3.7 µL; 20 mol equivalents). The reaction mixture was thoroughly mixed and allowed to incubate at room temperature for 2 h. The reaction mixture was exchanged into conjugation buffer (100 mM phosphate, 150 mM NaCl, pH 6.0) using a 0.5 mL Zeba desalting column pre-equilibrated with conjugation buffer and the OD/µL was determined. This prepared a 4FB modified 5'-amino-modified oligonucleotide that was used directly in the conjugation step.

3'-4FB-40mer Oligo-1 (30.8 µL; 5 mol equivalents) was added followed by addition of TurboLink™ Catalyst (14 µL (1/10 volume); 100 mM aniline, 100 mM phosphate, 150 mM NaCl, pH 6.0). The reaction mixture was incubated at room temperature for 2 hours.

The IMAC Zn-SepFast MAG Media (120 uL of a 50% slurry, Biotoolmics, UK) was prepped by addition of the beads 1.5 mL microcentrifuge tube, magnetizing the beads on a magnetic stand and the supernatant was removed. The beads were washed three times with binding buffer (200 µL; 100 mM phosphate, 150 mM NaCl; pH 6.0). Following removal of the final wash the entire volume (~110 µL) of the completed antibody-oligonucleotide conjugation reaction was added directly onto the bead pellet. The reaction/bead mixture was carefully mixed by swirling with a pipette tip for 30 seconds. The beads were allowed to settle for 15 min at room temperature (18-25° C.). The slurry was mixed again by swirling and allowed to settle for an additional 15 min. The tube was placed on a magnetic stand for 1 min to pellet the beads and the supernatant was gently removed and discarded. The bead pellet was washed three more times with 400 µL wash buffer discarding the supernatant each time.

The conjugate was then eluted and removed from the beads by adding 50 µL bead elution buffer (300 mM imidazole, 300 mM NaCl, 50 mM EDTA, 70 ug/mL (83.3 uM) (His)$_6$ peptide (SEQ ID NO: 1) to the bead pellet. The slurry was gently mixed by swirling with a pipet tip for 30 sec and incubate the settled slurry for 15 minutes mixing gently at 5 minute intervals. The tube was placed into the magnetic stand to allow the beads to pellet for 1 min. The supernatant containing the affinity purified antibody-oligonucleotide conjugate was transferred into a new 1.5 mL tube. The beads were eluted three more times with 50 µL elution buffer to obtain the maximum conjugate recovery. The combined eluants were buffer exchanged into storage buffer (PBS, 1 mM EDTA). Oligonucleotide concentration was determined spectrophotometrically by determining the conjugate's absorbance at 260 nm. Antibody concentration was determined using the BCA assay (ThermoPierce, Rockville, Ill.). Typical yields are 30-50% based on protein BCA assay. The molar substitution ratio is 2.0-2.5 oligonucleotides/antibody. The conjugates were further analyzed by gel electrophoresis using 12% Bis-Tris Gel (Invitrogen (Carlsbad, Calif.)) and visualized by

Example 7

Protocol for Preparation of an Antibody/Oligonucleotide Conjugate on a Solid Phase Support (Prospective)

MAC Zn-SepFast MAG Media (120 uL of a 50% slurry, Biotoolmics, UK) c be prepped by addition of the beads 1.5 mL microcentrifuge tube, magnetizing the beads on a magnetic stand and the supernatant can be removed. The beads can be washed three times with Binding Buffer (200 µL; 100 mM phosphate, 150 mM NaCl; pH 6.0). Antibody (100 ug) in 100 uL in Binding Buffer is added to the beads. The antibody/bead mixture can be carefully mixed by swirling with a pipette tip for 30 seconds. The beads can be allowed to settle for 15 min at room temperature (18-25° C.). The slurry can be mixed again by swirling and allowed to settle for an additional 15 min. The tube can be placed on a magnetic stand for 1 min to pellet the beads and the supernatant can be gently removed and discarded. The bead pellet can be washed three more times with 400 µL Modification Buffer discarding the supernatant each time. To the bead slurry can be added a 20 mg/mL solution sulfo-S-HyNic (20-50 mol equivalents) in Modification Buffer. The beads can be swirled and allowed to incubate at room temperature for 2 h. The bead reaction mixture can be diluted to 400 uL with Conjugation Buffer swirled and allowed to stand for 15 min. The tube can be placed on a magnetic stand for 1 min to pellet the beads and the supernatant can be gently removed and discarded. The bead pellet can be washed three more times with 400 µL Conjugation Buffer discarding the supernatant each time. To the beads can be added 4FB-oligonucleotide (3-5 equivalents) and a ¹⁄₁₀ volume of TurboLink buffer. The reaction mixture can be swirled and allowed to incubate at room temperature for 1-16 h. The tube can be placed on a magnetic stand for 1 min to pellet the beads and the supernatant can be gently removed and discarded. The beads can be washed with 25 mM sodium phosphate, 300 mM sodium chloride, 0.05% Tween-20, pH 7.5 4 times. The conjugate can be eluted from the beads with 25 mM EDTA, 300 mM NaCl, 250 mM Imidazole, 75 ug/mL HIS-6 peptide (SEQ ID NO: 1), pH 6.0, 4 times. The purified conjugate can be exchanged into 10 mM sodium phosphate, 149 mM sodium chloride, 1 mM EDTA, 0.05% sodium azide, pH 7.2.

Example 8

Protocol for Preparation and Purification of Protein/Oligonucleotide Conjugate (Prospective)

For example, a Streptavidin/oligonucleotide conjugate can be prepared and purified using the following protocol.

Step 1: To a solution of streptavidin (1000 uL of a 5 mg/mL solution; Roche Biosciences) in modification buffer can be added a solution of S-4FB (9.7 uL of a 10 mg/mL solution in anhydrous DMF; 10 mol equiv.). The reaction mixture can be gently vortexed and allowed to stand at room temperature for 1.5 h. The reaction mixture can be desalted into conjugation buffer using a 2 mL Zeba column pre-equilibrated with conjugation buffer.

Step 2: His-tag conjugation: To 4FB-streptavidin prepared in step 1 can be added HyNic-Peg2-His6-NH$_2$ ("His6" disclosed as SEQ ID NO: 1) (SoluLink Biosciences; 4.2 uL of a 20 mg/mL solution in conjugation buffer; 0.75 mol equivalent). The His6-StAv conjugate ("His6" disclosed as SEQ ID NO: 1) can be purified by adsorption of the conjugate using His-Tag Purification Chelating Agarose Beads (Agarose Bead Technologies (Tampa, Fla.) followed by washing to remove unconjugated streptavidin. The conjugate can be eluted off the beads using imidazole/EDTA buffer. The isolated HyNic-Peg2-streptavidin conjugate can be desalted into conjugation buffer using a 5 MWCO diafiltration apparatus to both desalt and remove unconjugated HyNic-Peg2-His6-NH$_2$ ("His6" disclosed as SEQ ID NO: 1).

Step 3: Preparation of HyNic-oligonucleotide: A 5'-amino-modified 38mer oligonucleotide can be exchanged and concentrated into modification buffer (100 mM phosphate, 150 mM NaCl, pH 7.4) using a 5K MWCO Vivaspin column (Sartorius Stedim, Purchase, N.Y.). The final concentration can be adjusted to 0.3 OD/uL. To the oligo in modification buffer (33.4 uL; 30 nmol) is added DMF (16.7 uL) and S-HyNic (11 uL of a 10 mg/mL solution in DMF; 15 equivalents; SoluLink Biosciences). The reaction mixture can be vortexed and allowed to stand at room temperature for 1.5 hours). The reaction mixture can be desalted into conjugation buffer (100 mM phosphate, 150 mM NaCl, pH 6.0) using a 5 K MWCO VivaSpin column. Resuspension into conjugation buffer and concentration can be repeated 3 times. The oligo concentration can be adjusted to 0.25 OD/uL.

Step 4: Oligo conjugation and conjugate purification: To the 4FB-StAv-His-tag conjugate in Conjugation Buffer prepared in Step 2 (1 mol equivalent) can be added HyNic-38mer oligonucleotide (2.0 mol equiv) in conjugation and ¹⁄₁₀ volume TurboLink catalyst. The reaction mixture can be incubated at room temperature for 2 hours and the 38mer oligonucleotide-StAv-His-tag conjugate can be purified by addition of the reaction mixture to Zinc-His-tag magnetic beads and incubated for 30 min to allow the conjugate to bind to the beads. The supernatant can be removed and the buffer (0.4 mL) can be added to the beads and the mixture can be gently mixed using a pipette, incubated for X min and supernatant can be removed. This washing procedure can be repeated 3 more times. The conjugate can be eluted from the beads by adding elution buffer (100 mM imidazole; EDTA; buffer) incubating for X minutes. The supernatant can be removed and collected in a separate tube. The elution procedure can be repeated three more times. The combined eluants can be exchanged into 5 mM EDTA, PBS using a 0.5 mL pre-equilibrated Zeba column.

What is claimed is:

1. A method for isolating antibody-oligonucleotide conjugates, comprising:
   i) introducing a modified antibody into a buffered solution, wherein the modified antibody includes a histidine-rich region;
   ii) conjugating the modified antibodies with at least one modified oligonucleotide at greater than 80% efficiency to form antibody-oligonucleotide conjugates; and
   iii) isolating the antibody-oligonucleotide conjugates from the conjugation solution by binding the conjugates to an immobilized binder, removing the unconjugated oligonucleotide in a wash step followed by release of the bound conjugate from the solid support.

2. The method of claim 1, wherein the immobilized binder comprises a metal ion.

3. The method of claim 2, wherein the metal ion is a transition metal ion.

4. The method of claim 3, wherein the transition metal ion is selected from the group comprising: nickel ion, zinc ion, copper ion, iron ion and cobalt ion.

5. The method of claim 1, wherein the immobilized binder comprises an immobilized antibody.

6. The method of claim 1, wherein conjugating efficiency is greater than 85%.

7. The method of claim 1, wherein the modified antibody is prepared from an IgG or IgM type antibody.

8. The method of claim 1, wherein the modified antibody comprises an antibody that has been prepared by attaching at least one moiety comprising a reactive linker capable of conjugating to a modified oligonucleotide.

9. The method of claim 1, wherein modified antibody further comprises a succinimidyl 6-hydrazinonicotinate acetone hydrazone modification.

10. The method of claim 1, wherein the isolated antibody-oligonucleotide conjugates comprise on average at least 2 modified oligonucleotides.

11. The method of claim 1, wherein the isolated antibody-oligonucleotide conjugates comprises a composition of antibody-oligonucleotide conjugates having on average between 1.0 and 2.5 modified oligonucleotides conjugated to the antibody.

12. A method for isolating antibody-oligonucleotide conjugates, comprising:
   i) introducing a modified antibody into a buffered solution;
   ii) conjugating the modified antibodies with at least one modified oligonucleotide at greater than 80% efficiency to form antibody-oligonucleotide conjugates; and
   iii) isolating the antibody-oligonucleotide conjugates from the conjugation solution by binding the conjugates to an immobilized binder, removing the unconjugated oligonucleotide in a wash step followed by release of the bound conjugate from the solid support,
wherein the immobilized binder comprises an organic chelator selected from the group comprising: iminodiacetic acid, nitrilotriacetic acid and bicinchoninic acid.

13. The method of claim 12, wherein conjugating efficiency is greater than 85%.

14. The method of claim 12, wherein the modified antibody is prepared from an IgG or IgM type antibody.

15. The method of claim 12, wherein the modified antibody comprises an antibody that has been prepared by attaching at least one moiety comprising a reactive linker capable of conjugating to a modified oligonucleotide.

16. The method of claim 12, wherein modified antibody further comprises a succinimidyl 6-hydrazinonicotinate acetone hydrazone modification.

17. The method of claim 12, wherein the isolated antibody-oligonucleotide conjugates comprise on average at least 2 modified oligonucleotides.

18. The method of claim 12, wherein the isolated antibody-oligonucleotide conjugates comprises a composition of antibody-oligonucleotide conjugates having on average between 1.0 and 2.5 modified oligonucleotides conjugated to the antibody.

19. A method for isolating antibody-oligonucleotide conjugates, comprising:
   i) introducing a modified antibody into a buffered solution, wherein the modified antibody comprises a molecular tag comprising a poly-histidine tag, a Flag Tag, a c-Myc-Tag, an S-tag, or a peptide tag;
   ii) conjugating the modified antibodies with at least one modified oligonucleotide at greater than 80% efficiency to form antibody-oligonucleotide conjugates; and
   iii) isolating the antibody-oligonucleotide conjugates from the conjugation solution by binding the conjugates to an immobilized binder, removing the unconjugated oligonucleotide in a wash step followed by release of the bound conjugate from the solid support.

20. The method of claim 19, wherein the immobilized antibody is complementary to the molecular tag that is bound to the modified antibody.

21. The method of claim 19, wherein the immobilized binder comprises a metal ion.

22. The method of claim 21, wherein the metal ion is a transition metal ion.

23. The method of claim 22, wherein the transition metal ion is selected from the group comprising: nickel ion, zinc ion, copper ion, iron ion and cobalt ion.

24. The method of claim 19, wherein the immobilized binder comprises an immobilized antibody.

25. The method of claim 19, wherein conjugating efficiency is greater than 85%.

26. The method of claim 19, wherein the modified antibody is prepared from an IgG or IgM type antibody.

27. The method of claim 19, wherein the modified antibody comprises an antibody that has been prepared by attaching at least one moiety comprising a reactive linker capable of conjugating to a modified oligonucleotide.

28. The method of claim 19, wherein modified antibody further comprises a succinimidyl 6-hydrazinonicotinate acetone hydrazone modification.

29. The method of claim 19, wherein the isolated antibody-oligonucleotide conjugates comprise on average at least 2 modified oligonucleotides.

30. The method of claim 19, wherein the isolated antibody-oligonucleotide conjugates comprises a composition of antibody-oligonucleotide conjugates having on average between 1.0 and 2.5 modified oligonucleotides conjugated to the antibody.

* * * * *

SEQUENCE LISTING

<160> NUMBER OF SEQ ID NOS: 3

<210> SEQ ID NO 1
<211> LENGTH: 6
<212> TYPE: PRT
<213> ORGANISM: Artificial Sequence

```
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gactgacgaa ccgctttgcc tgactgatcg ctaaatcgtg                            40

<210> SEQ ID NO 3
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ttgcatcgcc cttggactac gactgacgaa ccgctttgcc tgactgatcg ctaaatcgtg     60
```